US010470948B2

(12) United States Patent
Busam et al.

(10) Patent No.: US 10,470,948 B2
(45) Date of Patent: *Nov. 12, 2019

(54) THIN AND DRY DIAPER

(71) Applicant: The Procter & Gamble Company, Cincinnati, OH (US)

(72) Inventors: Ludwig Busam, Hünstetten (DE); Uwe Jurgen Becker, Euskirchen (DE); Michael Divo, Friedrichsdorf (DE); Bruno Johannes Ehrnsperger, Bad Soden (DE); Roland Engel, Sulzbach (DE); Torsten Lindner, Kronberg (DE); Siegfried Link, Schleiden (DE); Volker Maier, Cologne (DE); Sanaul Kabir Siddiquee, Brussels (DE); Gabriel Stiehl, Bad Soden (DE); Thomas Tombuelt-Meyer, Nettersheim (DE)

(73) Assignee: The Procter & Gamble Company, Cincinnati, OH (US)

(*) Notice: Subject to any disclaimer, the term of this patent is extended or adjusted under 35 U.S.C. 154(b) by 340 days.

This patent is subject to a terminal disclaimer.

(21) Appl. No.: 14/161,748

(22) Filed: Jan. 23, 2014

(65) Prior Publication Data

US 2014/0135726 A1    May 15, 2014

Related U.S. Application Data

(62) Division of application No. 11/973,811, filed on Oct. 10, 2007, now Pat. No. 8,674,170, which is a division
(Continued)

(51) Int. Cl.
A61F 13/15    (2006.01)
A61F 13/532    (2006.01)
(Continued)

(52) U.S. Cl.
CPC .... A61F 13/5323 (2013.01); A61F 13/15658 (2013.01); A61F 13/15699 (2013.01);
(Continued)

(58) Field of Classification Search
CPC .......... A61F 13/15; A61F 13/20; A61F 13/53; A61F 13/55; A61F 13/56
See application file for complete search history.

(56) References Cited

U.S. PATENT DOCUMENTS 1,733,997 A    10/1929 Marr
1,734,499 A    11/1929 Marinsky
(Continued)

FOREIGN PATENT DOCUMENTS

CA    2001370    4/1990
CA    2291997    6/2000
(Continued)

OTHER PUBLICATIONS

All Office Actions, U.S. Appl. No. 10/776,851.
(Continued)

Primary Examiner — Tatyana Zalukaeva
Assistant Examiner — Ilya Y Treyger
(74) Attorney, Agent, or Firm — Wednesday G. Shipp

(57) ABSTRACT

An absorbent article, preferably a disposable absorbent article such as a diaper, is disclosed having an absorbent core which imparts increased wearing comfort to the article and makes it thin and dry. The absorbent core useful for an absorbent article comprises a substrate layer, a discontinuous layer of absorbent material, and a layer of thermoplastic material. A second surface of the discontinuous layer of absorbent material is in at least partial contact with a first surface of the substrate layer. Portions of a second surface of the layer of thermoplastic material are in direct contact with the first surface of the substrate layer and portions of said
(Continued)

second surface of the layer of thermoplastic material are in direct contact with a first surface of the discontinuous layer of absorbent material. A process for providing a storage layer for an absorbent core useful in an absorbent article is further disclosed.

12 Claims, 5 Drawing Sheets

Related U.S. Application Data of application No. 10/776,839, filed on Feb. 11, 2004, now Pat. No. 7,744,576.

(51) Int. Cl.
*A61F 13/536* (2006.01)
*A61F 13/539* (2006.01)
*A61F 13/20* (2006.01)
*A61F 13/53* (2006.01)
*A61F 13/56* (2006.01)

(52) U.S. Cl.
CPC .......... *A61F 13/536* (2013.01); *A61F 13/539* (2013.01); *A61F 2013/5395* (2013.01); *A61F 2013/530547* (2013.01); *B32B 2310/024* (2013.01); *Y10T 156/10* (2015.01); *Y10T 156/1062* (2015.01)

(56) References Cited

U.S. PATENT DOCUMENTS

| | | |
|---|---|---|
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,003 A | 4/1957 | Morin |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lonberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,071,138 A | 1/1963 | Garcia |
| 3,180,335 A | 4/1965 | Duncan et al. |
| 3,207,158 A | 9/1965 | Yoshitake et al. |
| 3,227,160 A | 1/1966 | Joy |
| 3,386,442 A | 6/1968 | Sabee |
| 3,561,446 A | 2/1971 | Jones |
| 3,572,342 A | 3/1971 | Lindquist et al. |
| 3,572,432 A | 3/1971 | Burton |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 10/1974 | Sabee |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,287,153 A | 9/1981 | Towsend |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr et al. |
| 4,469,710 A | 9/1984 | Bielley et al. |
| 4,475,912 A | 10/1984 | Coates |
| 4,490,148 A | 12/1984 | Beckeström |
| 4,507,438 A | 3/1985 | Obayashi et al. |
| 4,515,595 A | 5/1985 | Kievie |
| 4,527,990 A | 7/1985 | Sigl |
| 4,541,871 A | 9/1985 | Obayashi et al. |
| 4,551,191 A | 11/1985 | Kock et al. |
| 4,573,986 A | 3/1986 | Minetola et al. |
| 4,578,072 A | 3/1986 | Lancaster |
| 4,578,702 A | 3/1986 | Campbell |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug et al. |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman et al. |
| 4,623,342 A | 11/1986 | Ito et al. |
| 4,624,666 A | 11/1986 | Derossett |
| 4,629,643 A | 12/1986 | Curro et al. |
| 4,636,207 A | 1/1987 | Buell |
| 4,641,381 A | 2/1987 | Heran et al. |
| 4,646,510 A | 3/1987 | McIntyre |
| 4,662,875 A | 5/1987 | Hirotsu et al. |
| 4,666,983 A | 5/1987 | Tsubakimoto et al. |
| 4,670,011 A | 6/1987 | Mesek |
| 4,670,012 A | 6/1987 | Johnson |

(56) References Cited

U.S. PATENT DOCUMENTS

| | | |
|---|---|---|
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,720,321 A | 1/1988 | Smith |
| 4,731,066 A | 3/1988 | Korpman |
| 4,731,070 A | 3/1988 | Koci |
| RE32,649 E | 4/1988 | Brandt et al. |
| 4,741,941 A | 5/1988 | Englebert et al. |
| 4,747,846 A | 5/1988 | Boland et al. |
| 4,753,648 A | 6/1988 | Jackson |
| 4,773,905 A | 9/1988 | Molee |
| 4,784,892 A | 11/1988 | Storey et al. |
| 4,785,996 A | 11/1988 | Ziecker et al. |
| 4,787,896 A | 11/1988 | Houghton et al. |
| 4,795,454 A | 1/1989 | Dragoo |
| 4,800,102 A | 1/1989 | Takada |
| 4,802,884 A | 2/1989 | Fröidh et al. |
| 4,806,408 A | 2/1989 | Pierre et al. |
| 4,806,598 A | 2/1989 | Morman |
| 4,808,176 A | 2/1989 | Kielpikowski |
| 4,808,178 A | 2/1989 | Aziz |
| 4,826,880 A | 5/1989 | Lesniak et al. |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,848,815 A | 7/1989 | Molloy |
| 4,861,652 A | 8/1989 | Lippert et al. |
| 4,869,724 A | 9/1989 | Scripps |
| 4,886,697 A | 12/1989 | Perdelwitz et al. |
| 4,888,231 A | 12/1989 | Angstadt |
| 4,892,528 A | 1/1990 | Suzuki et al. |
| 4,892,535 A | 1/1990 | Bjornberg |
| 4,892,536 A | 1/1990 | DesMarais et al. |
| 4,894,060 A | 1/1990 | Nestegard |
| 4,894,277 A | 1/1990 | Akasaki |
| 4,904,251 A | 2/1990 | Igaue et al. |
| 4,900,317 A | 3/1990 | Buell |
| 4,909,802 A | 3/1990 | Ahr et al. |
| 4,909,803 A | 3/1990 | Aziz et al. |
| 4,936,839 A | 6/1990 | Molee |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen et al. |
| 5,071,414 A | 8/1991 | Elliott |
| 5,072,687 A | 12/1991 | Mitchell |
| 5,085,654 A | 2/1992 | Buell |
| 5,087,255 A | 2/1992 | Sims et al. |
| 5,092,861 A | 3/1992 | Nomura et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger et al. |
| 5,147,345 A | 9/1992 | Young et al. |
| 5,149,334 A | 9/1992 | Roe et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,188,624 A | 2/1993 | Young et al. |
| 5,190,563 A | 3/1993 | Herron et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | Desmarais et al. |
| 5,269,775 A | 12/1993 | Freeland et al. |
| 5,281,683 A | 1/1994 | Yano et al. |
| H1298 H | 4/1994 | Ahr |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | LaVon et al. |
| 5,366,782 A | 11/1994 | Curro et al. |
| 5,382,610 A | 1/1995 | Harada et al. |
| 5,387,207 A | 2/1995 | Dyer et al. |
| 5,387,208 A | 2/1995 | Ashton et al. |
| 5,387,209 A | 2/1995 | Yamamoto et al. |
| 5,389,095 A | 2/1995 | Suzuki |
| 5,397,316 A | 3/1995 | Lavon et al. |
| 5,397,317 A | 3/1995 | Thomas |
| 5,399,175 A | 3/1995 | Glaug |
| 5,401,792 A | 3/1995 | Babu et al. |
| 5,409,771 A | 4/1995 | Dahmen et al. |
| H1440 H | 5/1995 | New et al. |
| 5,411,497 A | 5/1995 | Tanzer et al. |
| 5,415,644 A | 5/1995 | Enloe |
| 5,425,725 A | 6/1995 | Tanzer et al. |
| 5,429,630 A | 7/1995 | Beal et al. |
| 5,433,715 A | 7/1995 | Tanzer et al. |
| 5,451,219 A | 9/1995 | Suzuki |
| 5,451,442 A | 9/1995 | Pieniak |
| 5,460,622 A | 10/1995 | Dragoo et al. |
| 5,460,623 A | 10/1995 | Emenaker et al. |
| 5,462,541 A | 10/1995 | Bruemmer et al. |
| 5,476,458 A | 12/1995 | Glaug et al. |
| 5,486,166 A | 1/1996 | Bishop et al. |
| 5,486,167 A | 1/1996 | Dragoo et al. |
| 5,487,736 A | 1/1996 | Phan |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell et al. |
| 5,507,736 A | 4/1996 | Clear et al. |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Hines et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |

(56) References Cited

U.S. PATENT DOCUMENTS

| | | |
|---|---|---|
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,559,335 A | 9/1996 | Zing et al. |
| 5,560,878 A | 10/1996 | Dragoo et al. |
| 5,562,634 A | 10/1996 | Flumene et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,575,783 A | 11/1996 | Clear et al. |
| 5,580,411 A | 12/1996 | Nease et al. |
| 5,584,829 A | 12/1996 | Lavash et al. |
| 5,586,979 A | 12/1996 | Thomas |
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |
| 5,607,414 A | 3/1997 | Richards et al. |
| 5,607,537 A | 3/1997 | Johnson et al. |
| 5,607,760 A | 3/1997 | Roe |
| 5,609,587 A | 3/1997 | Roe |
| 5,609,588 A | 3/1997 | DiPalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur |
| 5,624,424 A | 4/1997 | Saisaka et al. |
| 5,625,222 A | 4/1997 | Yoneda et al. |
| 5,607,416 A | 5/1997 | Yamamoto et al. |
| 5,626,571 A | 5/1997 | Young et al. |
| 5,628,741 A | 5/1997 | Buell et al. |
| 5,628,845 A | 5/1997 | Murray et al. |
| 5,635,191 A | 6/1997 | Roe et al. |
| 5,635,271 A | 6/1997 | Zafiroglu |
| 5,637,106 A | 6/1997 | Mitchell |
| 5,643,238 A | 7/1997 | Baker |
| 5,643,243 A | 7/1997 | Klemp |
| 5,643,588 A | 7/1997 | Roe et al. |
| 5,649,914 A | 7/1997 | Glaug |
| 5,650,214 A | 7/1997 | Anderson |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,662,758 A | 9/1997 | Hamilton et al. |
| 5,669,894 A | 9/1997 | Goldman et al. |
| 5,674,215 A | 10/1997 | Ronnberg |
| 5,681,300 A | 10/1997 | Ahr |
| 5,683,374 A | 11/1997 | Yamamoto |
| 5,685,874 A | 11/1997 | Buell et al. |
| 5,690,624 A | 11/1997 | Sasaki et al. |
| 5,690,627 A | 11/1997 | Clear et al. |
| 5,691,035 A | 11/1997 | Chappell et al. |
| 5,691,036 A | 11/1997 | Chappell et al. |
| 5,695,488 A | 12/1997 | Sosalla |
| 5,700,254 A | 12/1997 | McDowall et al. |
| 5,702,376 A | 12/1997 | Glaug |
| 5,713,881 A | 2/1998 | Rezai et al. |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | McFall et al. |
| H1732 H | 6/1998 | Johnson |
| 5,762,641 A | 6/1998 | Bewick-Sonntag et al. |
| 5,766,388 A | 6/1998 | Pelley |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka |
| 5,830,202 A | 11/1998 | Bogdanski et al. |
| 5,833,678 A | 11/1998 | Ashton et al. |
| 5,837,789 A | 11/1998 | Stockhausen et al. |
| 5,840,404 A | 11/1998 | Graff |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mitzutani |
| 5,855,572 A | 1/1999 | Schmidt |
| 5,858,013 A | 1/1999 | Kling |
| 5,858,515 A | 1/1999 | Stokes et al. |
| 5,865,823 A | 2/1999 | Curro |
| 5,865,824 A | 2/1999 | Chen |
| 5,873,868 A | 2/1999 | Nakahata |
| 5,876,391 A | 3/1999 | Roe et al. |
| 5,879,751 A | 3/1999 | Bogdanski |
| 5,891,118 A | 4/1999 | Toyoshima |
| 5,891,544 A | 4/1999 | Chappell et al. |
| 5,897,545 A | 4/1999 | Kline et al. |
| 5,904,673 A | 5/1999 | Roe et al. |
| 5,925,439 A | 7/1999 | Haubach |
| 5,928,184 A | 7/1999 | Etheredge |
| 5,931,825 A | 8/1999 | Kuen et al. |
| 5,938,648 A | 8/1999 | Lavon et al. |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline et al. |
| 5,968,025 A | 10/1999 | Roe et al. |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |
| 6,054,631 A | 4/2000 | Gent |
| 6,056,732 A | 5/2000 | Fujioka et al. |
| 6,060,115 A | 5/2000 | Borowski et al. |
| 6,068,620 A | 5/2000 | Chmielewski |
| 6,080,909 A | 6/2000 | Osterdahl et al. |
| 6,083,210 A | 7/2000 | Young et al. |
| 6,090,994 A | 7/2000 | Chen |
| 6,091,336 A | 7/2000 | Zand |
| 6,093,474 A | 7/2000 | Sironi |
| 6,099,515 A | 8/2000 | Sugito |
| 6,102,892 A | 8/2000 | Putzer et al. |
| 6,103,814 A | 8/2000 | Van Drongelen et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak |
| 6,143,821 A | 11/2000 | Houben |

(56) References Cited

U.S. PATENT DOCUMENTS

| | | |
|---|---|---|
| 6,152,908 A | 11/2000 | Widlund |
| 6,156,023 A | 12/2000 | Yoshioka |
| 6,156,424 A | 12/2000 | Taylor |
| 6,160,197 A | 12/2000 | Lassen |
| 6,165,160 A | 12/2000 | Suzuki et al. |
| 6,174,302 B1 | 1/2001 | Kumasaka |
| 6,177,606 B1 | 1/2001 | Etheredge |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Rönnberg |
| 6,254,294 B1 | 7/2001 | Muhar |
| 6,258,996 B1 | 7/2001 | Goldman |
| 6,261,679 B1 | 7/2001 | Chen et al. |
| 6,264,639 B1 | 7/2001 | Sauer |
| 6,265,488 B1 | 7/2001 | Fujino et al. |
| 6,290,686 B1 | 9/2001 | Tanzer et al. |
| 6,306,122 B1 | 10/2001 | Narawa et al. |
| 6,315,765 B1 | 11/2001 | Datta |
| 6,319,239 B1 | 11/2001 | Daniels et al. |
| 6,322,552 B1 | 11/2001 | Blenke et al. |
| 6,325,787 B1 | 12/2001 | Roe et al. |
| 6,326,525 B1 | 12/2001 | Hamajima |
| 6,330,735 B1 | 12/2001 | Hahn et al. |
| 6,334,858 B1 | 1/2002 | Rönnberg et al. |
| 6,336,922 B1 | 1/2002 | Van Gompel et al. |
| 6,340,611 B1 | 1/2002 | Shimizu |
| 6,342,715 B1 | 1/2002 | Shimizu |
| 6,402,731 B1 | 1/2002 | Suprise et al. |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin et al. |
| 6,383,960 B1 | 5/2002 | Everett et al. |
| 6,394,989 B2 | 5/2002 | Mizutani |
| 6,403,857 B1 | 6/2002 | Gross et al. |
| 6,406,467 B1 | 6/2002 | Dilnik et al. |
| 6,409,883 B1 | 6/2002 | Makolin |
| 6,410,820 B1 | 6/2002 | McFall et al. |
| 6,410,822 B1 | 6/2002 | Mizutani |
| 6,402,729 B1 | 7/2002 | Boberg et al. |
| 6,413,248 B1 | 7/2002 | Mizutani |
| 6,413,249 B1 | 7/2002 | Turi et al. |
| 6,414,214 B1 | 7/2002 | Engelhardt et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Rönnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,034 B1 | 10/2002 | Schaefer et al. |
| 6,461,342 B2 | 10/2002 | Tanji et al. |
| 6,461,343 B1 | 10/2002 | Schaefer et al. |
| 6,472,478 B1 | 10/2002 | Funk et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen |
| 6,521,812 B1 | 2/2003 | Graef |
| 6,524,294 B1 | 2/2003 | Hilston et al. |
| 6,525,240 B1 | 2/2003 | Graef |
| 6,528,698 B2 | 3/2003 | Mizutani et al. |
| 6,529,860 B1 | 3/2003 | Strumolo et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LeMahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B2 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,129 B2 | 3/2004 | Ando et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,205 B2 | 4/2004 | Popp et al. |
| 6,716,441 B1 | 4/2004 | Roe et al. |
| 6,717,029 B2 | 4/2004 | Baker |
| 6,726,668 B2 | 4/2004 | Underhill et al. |
| 6,726,792 B1 | 4/2004 | Johnson et al. |
| 6,730,387 B2 | 5/2004 | Rezai et al. |
| 6,734,335 B1 | 5/2004 | Graef |
| 6,790,798 B1 | 9/2004 | Suzuki et al. |
| 6,802,834 B2 | 10/2004 | Melius et al. |
| 6,809,158 B2 | 10/2004 | Ikeuchi et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,830,800 B2 | 12/2004 | Curro et al. |
| 6,832,905 B2 | 12/2004 | Delzer et al. |
| 6,840,929 B2 | 1/2005 | Kurata |
| 6,846,374 B2 | 1/2005 | Popp |
| 6,858,771 B2 | 2/2005 | Yoshimasa |

(56) References Cited

U.S. PATENT DOCUMENTS

| | | | |
|---|---|---|---|
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 * | 4/2005 | Curro .................. B32B 37/144 |
| | | | 428/156 |
| 6,878,647 B1 | 4/2005 | Rezai |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,923,926 B2 | 8/2005 | Walter et al. |
| 6,926,703 B2 | 8/2005 | Sugito |
| 6,929,629 B2 | 8/2005 | Drevik et al. |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Henry et al. |
| 6,962,578 B1 | 11/2005 | Lavon |
| 6,962,645 B2 | 11/2005 | Graef |
| 6,965,058 B1 | 11/2005 | Raidel |
| 6,969,781 B2 | 11/2005 | Graef |
| 6,972,010 B2 | 12/2005 | Pesce et al. |
| 6,972,011 B2 | 12/2005 | Maeda et al. |
| 6,979,564 B2 | 12/2005 | Glucksmann et al. |
| 6,982,052 B2 | 1/2006 | Daniels et al. |
| 7,001,167 B2 | 2/2006 | Venturino |
| 7,014,632 B2 | 3/2006 | Takino et al. |
| 7,015,370 B2 | 3/2006 | Watanabe |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita |
| 7,067,711 B2 | 6/2006 | Kinoshita et al. |
| 7,073,373 B2 | 7/2006 | La Fortune |
| 7,078,583 B2 | 7/2006 | Kudo |
| 7,090,665 B2 | 8/2006 | Ohashi |
| 7,108,759 B2 | 9/2006 | You |
| 7,108,916 B2 | 9/2006 | Ehrnsperger et al. |
| 7,112,621 B2 | 9/2006 | Rohrbaugh et al. |
| 7,122,713 B2 | 10/2006 | Komatsu |
| 7,125,470 B2 | 10/2006 | Graef |
| 7,132,585 B2 | 11/2006 | Kudo |
| 7,147,628 B2 | 12/2006 | Drevik |
| 7,150,729 B2 | 12/2006 | Shimada |
| 7,154,019 B2 | 12/2006 | Mishima et al. |
| 7,160,281 B2 | 1/2007 | Leminh et al. |
| 7,163,528 B2 | 1/2007 | Christon et al. |
| 7,166,190 B2 | 1/2007 | Graef |
| 7,169,136 B2 | 1/2007 | Otsubo |
| 7,183,360 B2 | 2/2007 | Daniel et al. |
| 7,189,888 B2 | 3/2007 | Wang et al. |
| 7,196,241 B2 | 3/2007 | Kinoshita |
| 7,199,211 B2 | 4/2007 | Popp et al. |
| 7,204,830 B2 | 4/2007 | Mishima |
| 7,207,978 B2 | 4/2007 | Takino |
| 7,219,403 B2 | 5/2007 | Miyamoto et al. |
| 7,220,251 B2 | 5/2007 | Otsubo et al. |
| 7,241,280 B2 | 7/2007 | Christen et al. |
| 7,250,481 B2 | 7/2007 | Jaworek et al. |
| 7,252,657 B2 | 8/2007 | Mishima |
| 7,265,258 B2 | 9/2007 | Hamilton |
| 7,270,651 B2 | 9/2007 | Adams et al. |
| 7,285,178 B2 | 10/2007 | Mischler et al. |
| 7,306,582 B2 | 12/2007 | Adams et al. |
| 7,311,696 B2 | 12/2007 | Christen et al. |
| 7,311,968 B2 | 12/2007 | Ehrnsperger et al. |
| 7,312,372 B2 | 12/2007 | Miyama |
| 7,318,820 B2 | 1/2008 | LaVon et al. |
| 7,329,244 B2 | 2/2008 | Otsubo |
| 7,329,246 B2 | 2/2008 | Kinoshita |
| 7,335,810 B2 | 2/2008 | Yoshimasa et al. |
| 7,377,914 B2 | 5/2008 | LaVon |
| 7,429,689 B2 | 9/2008 | Chen |
| 7,435,244 B2 | 10/2008 | Schroer et al. |
| 7,465,373 B2 | 12/2008 | Graef |
| 7,500,969 B2 | 3/2009 | Mishima |
| 7,504,552 B2 | 3/2009 | Tamura |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi |
| 7,550,646 B2 | 6/2009 | Tamura |
| 7,563,257 B2 | 7/2009 | Nakajima |
| 7,588,561 B2 | 9/2009 | Kenmochi |
| 7,594,904 B2 | 9/2009 | Rosenfeld |
| 7,598,428 B2 | 10/2009 | Gustavsson et al. |
| 7,625,363 B2 | 12/2009 | Yoshimasa |
| 7,641,642 B2 | 1/2010 | Murai et al. |
| 7,648,490 B2 | 1/2010 | Kuroda |
| 7,652,111 B2 | 1/2010 | Hermeling et al. |
| 7,666,173 B2 | 2/2010 | Mishima |
| 7,666,174 B2 | 2/2010 | Kawakami et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld |
| 7,696,402 B2 | 4/2010 | Nishikawa |
| 7,708,725 B2 | 5/2010 | Tamagawa |
| 7,717,150 B2 | 5/2010 | Manabe |
| 7,718,844 B2 | 5/2010 | Olson |
| 7,722,587 B2 | 5/2010 | Suzuki et al. |
| 7,722,590 B2 | 5/2010 | Tsuji |
| 7,727,217 B2 | 6/2010 | Hancock-Cooke |
| 7,736,351 B2 | 6/2010 | Nigam |
| 7,737,324 B2 | 6/2010 | LaVon et al. |
| 7,744,576 B2 | 6/2010 | Busam et al. |
| 7,744,578 B2 | 6/2010 | Tanio et al. |
| 7,750,203 B2 | 7/2010 | Busam et al. |
| 7,754,822 B2 | 7/2010 | Daniel et al. |
| 7,754,940 B2 | 7/2010 | Brisebois |
| 7,759,540 B2 | 7/2010 | Litvay et al. |
| 7,763,004 B2 | 7/2010 | Beck |
| 7,767,875 B2 | 8/2010 | Olson |
| 7,767,876 B2 | 8/2010 | Davis et al. |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld |
| 7,825,291 B2 | 11/2010 | Elfsberg et al. |
| 7,838,722 B2 | 11/2010 | Blessing et al. |
| 7,850,672 B2 | 12/2010 | Guidotti et al. |
| 7,851,667 B2 | 12/2010 | Becker et al. |
| 7,855,314 B2 | 12/2010 | Hanao |
| 7,857,797 B2 | 12/2010 | Kudo |
| 7,858,842 B2 | 12/2010 | Komatsu |
| 7,884,259 B2 | 2/2011 | Hanao |
| 7,888,549 B2 | 2/2011 | Jansson et al. |
| 7,910,797 B2 | 3/2011 | Nandrea |
| 7,931,636 B2 | 4/2011 | LaVon et al. |
| 7,935,207 B2 | 5/2011 | Zhao |
| 7,935,861 B2 | 5/2011 | Suzuki |
| 7,938,813 B2 | 5/2011 | Wang et al. |
| 7,942,858 B2 | 5/2011 | Francoeur |
| 7,951,126 B2 | 5/2011 | Nanjyo |
| 7,959,620 B2 | 6/2011 | Miura et al. |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe |
| 8,124,828 B2 | 2/2012 | Kline et al. |
| 8,133,212 B2 | 3/2012 | Takada |
| 8,148,598 B2 | 4/2012 | Tsang et al. |
| 8,163,124 B2 | 4/2012 | Moriura et al. |
| 8,167,862 B2 | 5/2012 | Digiacomantonio et al. |
| 8,173,858 B2 | 5/2012 | Kuroda |
| 8,178,747 B2 | 5/2012 | Venturino et al. |
| 8,183,430 B2 | 5/2012 | Hakansson et al. |

(56) References Cited

U.S. PATENT DOCUMENTS

| | | |
|---|---|---|
| 8,186,296 B2 | 5/2012 | Brown et al. |
| 8,187,239 B2 | 5/2012 | LaVon et al. |
| 8,187,240 B2 | 5/2012 | Busam et al. |
| 8,198,506 B2 | 6/2012 | Venturino et al. |
| 8,211,815 B2 | 7/2012 | Baker |
| 8,236,715 B2 | 8/2012 | Schmidt et al. |
| 8,237,012 B2 | 8/2012 | Miyama |
| 8,246,594 B2 | 8/2012 | Sperl |
| 8,258,367 B2 | 9/2012 | Lawson et al. |
| 8,268,424 B1 | 9/2012 | Suzuki |
| 8,273,943 B2 | 9/2012 | Noda |
| 8,282,617 B2 | 10/2012 | Kaneda |
| 8,283,516 B2 | 10/2012 | Litvay |
| 8,317,766 B2 | 11/2012 | Naoto |
| 8,317,768 B2 | 11/2012 | Larsson |
| 8,319,005 B2 | 11/2012 | Becker et al. |
| 8,343,123 B2 | 1/2013 | Noda |
| 8,343,296 B2 | 1/2013 | Blessing et al. |
| 8,360,977 B2 | 1/2013 | Marttila |
| 8,361,047 B2 | 1/2013 | Mukai |
| 8,377,025 B2 | 2/2013 | Nakajima |
| 8,450,555 B2 | 5/2013 | Nahn et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,566 B2 | 10/2013 | Jackels et al. |
| 8,569,571 B2 | 10/2013 | Kline et al. |
| 8,581,019 B2 | 11/2013 | Carlucci et al. |
| 8,603,058 B2 | 12/2013 | Sprerl et al. |
| 8,604,270 B2 | 12/2013 | Venturino et al. |
| 8,633,347 B2 | 1/2014 | Bianco et al. |
| 8,664,468 B2 | 3/2014 | Lawson et al. |
| 8,734,417 B2 | 5/2014 | LaVon et al. |
| 8,766,031 B2 | 7/2014 | Becker et al. |
| 8,772,570 B2 | 7/2014 | Kawakami et al. |
| 8,784,594 B2 | 7/2014 | Blessing et al. |
| 8,785,715 B2 | 7/2014 | Wright et al. |
| 8,791,318 B2 | 7/2014 | Becker et al. |
| 8,936,584 B2 | 1/2015 | Zander et al. |
| 9,056,034 B2 | 6/2015 | Akiyama |
| 9,326,896 B2 | 5/2016 | Schaefer et al. |
| 2001/0007065 A1 | 7/2001 | Blanchard |
| 2001/0008964 A1 | 7/2001 | Kurata et al. |
| 2001/0016548 A1 | 8/2001 | Kugler et al. |
| 2001/0020157 A1 | 9/2001 | Mizutani |
| 2001/0037101 A1 | 11/2001 | Allan et al. |
| 2001/0044610 A1 | 11/2001 | Kim |
| 2002/0007167 A1 | 1/2002 | Dan |
| 2002/0007169 A1 | 1/2002 | Graef et al. |
| 2002/0016122 A1 | 2/2002 | Curro et al. |
| 2002/0016579 A1 | 2/2002 | Stenberg |
| 2002/0045881 A1 | 4/2002 | Kusibojoska et al. |
| 2002/0056516 A1 | 5/2002 | Ochi |
| 2002/0058919 A1 | 5/2002 | Hamilton et al. |
| 2002/0062112 A1 | 5/2002 | Mizutani |
| 2002/0062115 A1 | 5/2002 | Wada et al. |
| 2002/0062116 A1 | 5/2002 | Mizutani et al. |
| 2002/0065498 A1 | 5/2002 | Ohashi |
| 2002/0072471 A1 | 6/2002 | Ikeuchi et al. |
| 2002/0082575 A1 | 6/2002 | Dan |
| 2002/0087139 A1 | 7/2002 | Popp et al. |
| 2002/0095126 A1 | 7/2002 | Inoue et al. |
| 2002/0095127 A1 | 7/2002 | Fish et al. |
| 2002/0102392 A1 | 8/2002 | Fish et al. |
| 2002/0115969 A1 | 8/2002 | Maeda et al. |
| 2002/0115972 A1 | 8/2002 | Dabi et al. |
| 2002/0123728 A1 | 9/2002 | Graef et al. |
| 2002/0123848 A1 | 9/2002 | Schneiderman et al. |
| 2002/0151634 A1 | 10/2002 | Rohrbaugh et al. |
| 2002/0151861 A1 | 10/2002 | Klemp et al. |
| 2002/0173767 A1 | 11/2002 | Popp et al. |
| 2002/0192366 A1 | 12/2002 | Cramer et al. |
| 2002/0197695 A1 | 12/2002 | Glucksmann et al. |
| 2003/0036741 A1 | 2/2003 | Abba et al. |
| 2003/0078553 A1 | 4/2003 | Wada |
| 2003/0084983 A1 | 5/2003 | Rangachari et al. |
| 2003/0088223 A1 | 5/2003 | Vogt et al. |
| 2003/0105190 A1 | 6/2003 | Diehl et al. |
| 2003/0109839 A1 | 6/2003 | Costae et al. |
| 2003/0114811 A1 | 6/2003 | Christen et al. |
| 2003/0114816 A1 | 6/2003 | Underhill |
| 2003/0114818 A1 | 6/2003 | Benecke et al. |
| 2003/0115969 A1 | 6/2003 | Koyano |
| 2003/0120235 A1 | 6/2003 | Boulanger |
| 2003/0120249 A1 | 6/2003 | Wulz et al. |
| 2003/0135176 A1 | 7/2003 | Delzer et al. |
| 2003/0135181 A1 | 7/2003 | Chen et al. |
| 2003/0135182 A1 | 7/2003 | Woon et al. |
| 2003/0139712 A1 | 7/2003 | Dodge |
| 2003/0139715 A1 | 7/2003 | Dodge |
| 2003/0139718 A1 | 7/2003 | Graef |
| 2003/0144642 A1 | 7/2003 | Dopps |
| 2003/0144644 A1 | 7/2003 | Murai et al. |
| 2003/0148684 A1 | 8/2003 | Cramer et al. |
| 2003/0148694 A1 | 8/2003 | Ghiam |
| 2003/0158530 A1 | 8/2003 | Diehl et al. |
| 2003/0158531 A1 | 8/2003 | Chmielewski |
| 2003/0158532 A1 | 8/2003 | Magee et al. |
| 2003/0167045 A1 | 9/2003 | Graef |
| 2003/0171727 A1 | 9/2003 | Graef |
| 2003/0208175 A1 | 11/2003 | Gross |
| 2003/0225385 A1 | 12/2003 | Glaug |
| 2003/0233082 A1 | 12/2003 | Kline et al. |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett |
| 2004/0063367 A1 | 4/2004 | Dodge |
| 2004/0064113 A1 | 4/2004 | Erdman |
| 2004/0064115 A1 | 4/2004 | Arora |
| 2004/0064116 A1 | 4/2004 | Arora |
| 2004/0064125 A1 | 4/2004 | Justmann et al. |
| 2004/0065420 A1 | 4/2004 | Graef |
| 2004/0082928 A1 | 4/2004 | Pesce et al. |
| 2004/0097895 A1 | 5/2004 | Busam et al. |
| 2004/0122411 A1 | 6/2004 | Hancock-Cooke |
| 2004/0127131 A1 | 7/2004 | Potnis |
| 2004/0127871 A1 | 7/2004 | Odorzynski |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko et al. |
| 2004/0162536 A1 | 8/2004 | Becker et al. |
| 2004/0167486 A1 | 8/2004 | Busam et al. |
| 2004/0167489 A1 | 8/2004 | Kellenberger et al. |
| 2004/0170813 A1 | 9/2004 | Digiacomantonio et al. |
| 2004/0193127 A1 | 9/2004 | Hansson |
| 2004/0215160 A1 | 10/2004 | Chmielewski |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0236455 A1 | 11/2004 | Woltman et al. |
| 2004/0249355 A1 | 12/2004 | Tanio et al. |
| 2004/0260259 A1 | 12/2004 | Baker |
| 2005/0004543 A1 | 1/2005 | Schroer et al. |
| 2005/0004548 A1 | 1/2005 | Otsubo et al. |
| 2005/0008839 A1 | 1/2005 | Cramer et al. |
| 2005/0018258 A1 | 1/2005 | Miyagi |
| 2005/0038401 A1 | 2/2005 | Suzuki et al. |
| 2005/0070867 A1 | 3/2005 | Beruda et al. |
| 2005/0085784 A1 | 4/2005 | LeMinh et al. |
| 2005/0090789 A1 | 4/2005 | Graef |
| 2005/0101929 A1 | 5/2005 | Waksmundzki et al. |
| 2005/0137543 A1 | 6/2005 | Underhill et al. |
| 2005/0148258 A1 | 7/2005 | Chakravarty |
| 2005/0148961 A1 | 7/2005 | Sosalla et al. |
| 2005/0148990 A1 | 7/2005 | Shimoe |
| 2005/0154363 A1 | 7/2005 | Minato |
| 2005/0159720 A1 | 7/2005 | Gentilcore et al. |
| 2005/0165208 A1 | 7/2005 | Popp et al. |
| 2005/0171499 A1 | 8/2005 | Nigam et al. |

(56) References Cited

U.S. PATENT DOCUMENTS

| | | |
|---|---|---|
| 2005/0176910 A1 | 8/2005 | Jaworek et al. |
| 2005/0203475 A1 | 9/2005 | LaVon et al. |
| 2005/0215752 A1 | 9/2005 | Popp et al. |
| 2005/0217791 A1 | 10/2005 | Costello et al. |
| 2005/0229543 A1 | 10/2005 | Tippey |
| 2005/0234414 A1 | 10/2005 | Liu et al. |
| 2005/0245684 A1 | 11/2005 | Daniel et al. |
| 2005/0288645 A1 | 12/2005 | LaVon |
| 2005/0288646 A1 | 12/2005 | LaVon |
| 2006/0004334 A1 | 1/2006 | Schlinz et al. |
| 2006/0021695 A1 | 2/2006 | Blessing et al. |
| 2006/0024433 A1 | 2/2006 | Blessing et al. |
| 2006/0069367 A1 | 3/2006 | Waksmundzki et al. |
| 2006/0069371 A1 | 3/2006 | Ohashi et al. |
| 2006/0073969 A1 | 4/2006 | Torii et al. |
| 2006/0081348 A1 | 4/2006 | Graef |
| 2006/0129114 A1 | 6/2006 | Mason et al. |
| 2006/0142724 A1 | 6/2006 | Watanabe |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt et al. |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo |
| 2006/0202380 A1 | 9/2006 | Bentley |
| 2006/0206091 A1 | 9/2006 | Cole |
| 2006/0211828 A1 | 9/2006 | Daniel et al. |
| 2006/0240229 A1 | 10/2006 | Ehrnsperger et al. |
| 2006/0264860 A1 | 11/2006 | Beck |
| 2006/0264861 A1 | 11/2006 | Lavon et al. |
| 2006/0271010 A1 | 11/2006 | LaVon et al. |
| 2007/0027436 A1 | 2/2007 | Nakagawa et al. |
| 2007/0032770 A1 | 2/2007 | Lavon et al. |
| 2007/0043191 A1 | 2/2007 | Hermeling et al. |
| 2007/0043330 A1 | 2/2007 | Lankhof et al. |
| 2007/0044903 A1 | 3/2007 | Wisneski et al. |
| 2007/0049892 A1 | 3/2007 | Lord et al. |
| 2007/0049897 A1 | 3/2007 | LaVon et al. |
| 2007/0073253 A1 | 3/2007 | Miyama |
| 2007/0078422 A1 | 4/2007 | Glaug |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto |
| 2007/0118087 A1 | 5/2007 | Flohr et al. |
| 2007/0123834 A1 | 5/2007 | McDowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug |
| 2007/0219521 A1 | 9/2007 | Hird et al. |
| 2007/0219523 A1 | 9/2007 | Bruun |
| 2007/0244455 A1 | 10/2007 | Hansson et al. |
| 2007/0246147 A1 | 10/2007 | Venturino et al. |
| 2007/0255245 A1 | 11/2007 | Asp et al. |
| 2007/0282288 A1 | 12/2007 | Noda |
| 2007/0282290 A1 | 12/2007 | Cole |
| 2007/0282291 A1 | 12/2007 | Cole |
| 2008/0027402 A1 | 1/2008 | Schmidt et al. |
| 2008/0032035 A1 | 2/2008 | Schmidt et al. |
| 2008/0091159 A1 | 4/2008 | Carlucci et al. |
| 2008/0119810 A1 | 5/2008 | Kuroda |
| 2008/0125735 A1 | 5/2008 | Busam et al. |
| 2008/0132864 A1 | 6/2008 | Lawson et al. |
| 2008/0208154 A1 | 8/2008 | Oetjen et al. |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto |
| 2008/0268194 A1 | 10/2008 | Kim et al. |
| 2008/0274227 A1 | 11/2008 | Boatman et al. |
| 2008/0281287 A1 | 11/2008 | Marcelo |
| 2008/0294140 A1 | 11/2008 | Ecker et al. |
| 2008/0312617 A1 | 12/2008 | Hundorf et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312627 A1 | 12/2008 | Takeuchi |
| 2008/0312628 A1 | 12/2008 | Hundorf et al. |
| 2009/0023848 A1 | 1/2009 | Ahmed et al. |
| 2009/0056867 A1 | 3/2009 | Moriura et al. |
| 2009/0062760 A1 | 3/2009 | Wright et al. |
| 2009/0112173 A1 | 4/2009 | Bissah |
| 2009/0112175 A1 | 4/2009 | Bissah et al. |
| 2009/0157022 A1 | 6/2009 | Macdonald |
| 2009/0192035 A1 | 7/2009 | Stueven et al. |
| 2009/0240220 A1 | 9/2009 | Macdonald |
| 2009/0247977 A1 | 10/2009 | Takeuchi |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | Macdonald |
| 2009/0306618 A1 | 12/2009 | Kudo |
| 2009/0318884 A1 | 12/2009 | Meyer et al. |
| 2009/0326494 A1 | 12/2009 | Uchida et al. |
| 2010/0051166 A1 | 3/2010 | Hundorf et al. |
| 2010/0062165 A1 | 3/2010 | Suzuki |
| 2010/0062934 A1 | 3/2010 | Suzuki |
| 2010/0063470 A1 | 3/2010 | Suzuki |
| 2010/0068520 A1 | 3/2010 | Stueven et al. |
| 2010/0100065 A1 | 4/2010 | Bianco |
| 2010/0115237 A1 | 5/2010 | Brewer et al. |
| 2010/0121296 A1 | 5/2010 | Noda |
| 2010/0137773 A1 | 6/2010 | Gross |
| 2010/0137823 A1 | 6/2010 | Corneliusson |
| 2010/0198179 A1 | 8/2010 | Noda |
| 2010/0228210 A1 | 9/2010 | Busam et al. |
| 2010/0241096 A1 | 9/2010 | LaVon et al. |
| 2010/0241097 A1 | 9/2010 | Nigam et al. |
| 2010/0262099 A1 | 10/2010 | Klofta |
| 2010/0262104 A1 | 10/2010 | Carlucci et al. |
| 2010/0274208 A1 | 10/2010 | Gabrielii |
| 2010/0274210 A1 | 10/2010 | Noda |
| 2010/0312208 A1 | 12/2010 | Bond et al. |
| 2010/0324521 A1 | 12/2010 | Mukai |
| 2010/0324523 A1 | 12/2010 | Mukai |
| 2011/0041999 A1 | 2/2011 | Hundorf et al. |
| 2011/0060301 A1 | 3/2011 | Nishikawa et al. |
| 2011/0060303 A1 | 3/2011 | Bissah |
| 2011/0066127 A1 | 3/2011 | Kuwano |
| 2011/0071486 A1 | 3/2011 | Harada |
| 2011/0092944 A1 | 4/2011 | Sagisaka |
| 2011/0112498 A1 | 5/2011 | Nhan et al. |
| 2011/0125120 A1 | 5/2011 | Nishitani |
| 2011/0130732 A1 | 6/2011 | Jackels et al. |
| 2011/0130737 A1 | 6/2011 | Sagisaka |
| 2011/0137276 A1 | 6/2011 | Yoshikawa |
| 2011/0144602 A1 | 6/2011 | Long |
| 2011/0144604 A1 | 6/2011 | Noda |
| 2011/0144606 A1 | 6/2011 | Nandrea |
| 2011/0152813 A1 | 6/2011 | Ellingson |
| 2011/0166540 A1 | 7/2011 | Yang et al. |
| 2011/0172630 A1 | 7/2011 | Nomoto |
| 2011/0174430 A1 | 7/2011 | Zhao |
| 2011/0196330 A1 | 8/2011 | Hammons et al. |
| 2011/0208147 A1 | 8/2011 | Kawakami et al. |
| 2011/0250413 A1 | 10/2011 | Lu et al. |
| 2011/0268932 A1 | 11/2011 | Catalan et al. |
| 2011/0274834 A1 | 11/2011 | Brown et al. |
| 2011/0288513 A1 | 11/2011 | Hundorf et al. |
| 2011/0288514 A1 | 11/2011 | Kuroda |
| 2011/0295222 A1 | 12/2011 | Becker et al. |
| 2011/0319846 A1 | 12/2011 | Rinnert et al. |
| 2011/0319848 A1 | 12/2011 | McKiernan et al. |
| 2011/0319851 A1 | 12/2011 | Kudo |

(56) References Cited

U.S. PATENT DOCUMENTS

| | | | |
|---|---|---|---|
| 2012/0004633 A1 | 1/2012 | Marcelo | |
| 2012/0016326 A1 | 1/2012 | Brennan et al. | |
| 2012/0022479 A1 | 1/2012 | Cotton | |
| 2012/0035566 A1 | 2/2012 | Sagisaka | |
| 2012/0035576 A1 | 2/2012 | Ichikawa | |
| 2012/0064792 A1 | 3/2012 | Bauduin | |
| 2012/0071848 A1 | 3/2012 | Zhang | |
| 2012/0165771 A1 | 6/2012 | Ruman et al. | |
| 2012/0175056 A1 | 7/2012 | Tsang | |
| 2012/0184934 A1 | 7/2012 | Venturino | |
| 2012/0232514 A1 | 9/2012 | Baker | |
| 2012/0238977 A1 | 9/2012 | Oku | |
| 2012/0253306 A1 | 10/2012 | Otsubo | |
| 2012/0256750 A1 | 10/2012 | Novak | |
| 2012/0271262 A1 | 10/2012 | Venturino | |
| 2012/0312491 A1 | 12/2012 | Jackels et al. | |
| 2012/0316046 A1 | 12/2012 | Jackels et al. | |
| 2012/0316523 A1 | 12/2012 | Hippe et al. | |
| 2012/0316526 A1 | 12/2012 | Rosati et al. | |
| 2012/0316527 A1 | 12/2012 | Rosati et al. | |
| 2012/0316528 A1 | 12/2012 | Kreuzer et al. | |
| 2012/0316529 A1 | 12/2012 | Kreuzer et al. | |
| 2012/0323195 A1 | 12/2012 | Ehrnsperger et al. | |
| 2012/0323201 A1 | 12/2012 | Bissah | |
| 2012/0323202 A1 | 12/2012 | Bissah | |
| 2013/0035656 A1 | 2/2013 | Moriya et al. | |
| 2013/0041334 A1 | 2/2013 | Prioleau | |
| 2013/0178811 A1 | 7/2013 | Kikuchi et al. | |
| 2013/0211354 A1 | 8/2013 | Tsuji et al. | |
| 2013/0211358 A1 | 8/2013 | Kikkawa et al. | |
| 2013/0218115 A1 | 8/2013 | Katsuragawa et al. | |
| 2013/0226119 A1 | 8/2013 | Katsuragawa et al. | |
| 2013/0226120 A1 | 8/2013 | Van De Maele | |
| 2013/0310784 A1 | 11/2013 | Bryant et al. | |
| 2014/0005622 A1 | 1/2014 | Wirtz et al. | |
| 2014/0005623 A1 | 1/2014 | Wirtz et al. | |
| 2014/0027066 A1 | 1/2014 | Jackels et al. | |
| 2014/0039437 A1 | 2/2014 | Van De Maele | |
| 2014/0045683 A1 | 2/2014 | Loick et al. | |
| 2014/0102183 A1 | 4/2014 | Agami et al. | |
| 2014/0121623 A1 | 5/2014 | Kirby et al. | |
| 2014/0142531 A1 | 5/2014 | Sasayama et al. | |
| 2014/0163500 A1 | 6/2014 | Roe et al. | |
| 2014/0163501 A1 | 6/2014 | Ehrnsperger et al. | |
| 2014/0163502 A1 | 6/2014 | Arizti et al. | |
| 2014/0163503 A1 | 6/2014 | Arizti et al. | |
| 2014/0163506 A1 | 6/2014 | Roe et al. | |
| 2014/0163511 A1 | 6/2014 | Roe et al. | |
| 2014/0171893 A1 | 6/2014 | Lawson et al. | |
| 2014/0318694 A1 | 10/2014 | Blessing et al. | |
| 2014/0324007 A1 | 10/2014 | Hundorf et al. | |
| 2014/0324008 A1 | 10/2014 | Hundorf et al. | |
| 2015/0065981 A1 | 3/2015 | Roe et al. | |
| 2015/0065986 A1 | 3/2015 | Blessing et al. | |
| 2015/0080837 A1 | 3/2015 | Rosati et al. | |
| 2015/0080839 A1 | 3/2015 | Trapp et al. | |
| 2015/0173967 A1 | 6/2015 | Kreuzer et al. | |
| 2015/0173968 A1 | 6/2015 | Joseph | |
| 2015/0250662 A1 | 9/2015 | Isele et al. | |

FOREIGN PATENT DOCUMENTS

| | | | |
|---|---|---|---|
| CA | 2308961 | | 11/2000 |
| CA | 2487027 | | 12/2003 |
| CA | 2561521 | | 3/2007 |
| CA | 2630713 | | 11/2008 |
| CA | 2636673 | | 1/2009 |
| CA | 2712563 | | 8/2010 |
| CA | 2702001 | | 10/2010 |
| CN | 1238171 | A | 12/1999 |
| CN | 2362468 | Y | 2/2000 |
| CN | 1371671 | | 2/2001 |
| CN | 2527254 | Y | 12/2002 |
| CN | 2535020 | Y | 2/2003 |
| CN | 2548609 | Y | 5/2003 |
| CN | 1539391 | | 10/2004 |
| CN | 1939242 | | 4/2007 |
| CN | 101292930 | | 10/2008 |
| CN | 201263750 | | 7/2009 |
| CN | 201591689 | | 9/2010 |
| CN | 201855366 | U | 6/2011 |
| DE | 3205931 | C2 | 9/1983 |
| DE | 3608114 | A1 | 9/1987 |
| DE | 19732499 | | 2/1999 |
| DE | 10204937 | A1 | 8/2003 |
| EP | 083022 | | 7/1983 |
| EP | 0 149 880 | A2 | 7/1985 |
| EP | 149880 | | 7/1985 |
| EP | 0 203 289 | A2 | 12/1986 |
| EP | 203289 | | 12/1986 |
| EP | 0206208 | | 12/1986 |
| EP | 209561 | B1 | 1/1987 |
| EP | 297411 | B1 | 1/1989 |
| EP | 304957 | | 3/1989 |
| EP | 374542 | | 6/1990 |
| EP | 394274 | | 10/1990 |
| EP | 0403832 | | 12/1990 |
| EP | 481322 | B1 | 4/1992 |
| EP | 530438 | | 3/1993 |
| EP | 547847 | | 6/1993 |
| EP | 555346 | | 8/1993 |
| EP | 559476 | | 9/1993 |
| EP | 591647 | B2 | 4/1994 |
| EP | 597273 | B1 | 5/1994 |
| EP | 601610 | B2 | 6/1994 |
| EP | 632068 | | 1/1995 |
| EP | 0 640 330 | A1 | 3/1995 |
| EP | 0668066 | | 9/1995 |
| EP | 685214 | | 12/1995 |
| EP | 687453 | | 12/1995 |
| EP | 0689817 | | 1/1996 |
| EP | 0691133 | | 1/1996 |
| EP | 0700673 | | 3/1996 |
| EP | 0394274 | | 7/1996 |
| EP | 724418 | | 8/1996 |
| EP | 725613 | | 8/1996 |
| EP | 725615 | | 8/1996 |
| EP | 725616 | | 8/1996 |
| EP | 758543 | | 2/1997 |
| EP | 0761194 | | 3/1997 |
| EP | 769284 | | 4/1997 |
| EP | 0781537 | | 7/1997 |
| EP | 783877 | B1 | 7/1997 |
| EP | 787472 | | 8/1997 |
| EP | 788874 | B1 | 8/1997 |
| EP | 796068 | | 9/1997 |
| EP | 799004 | | 10/1997 |
| EP | 822794 | B1 | 2/1998 |
| EP | 826351 | | 3/1998 |
| EP | 844861 | | 6/1998 |
| EP | 0737055 | | 8/1998 |
| EP | 863733 | | 9/1998 |
| EP | 971751 | | 9/1998 |
| EP | 0875224 | | 11/1998 |
| EP | 875224 | A1 | 11/1998 |
| EP | 880955 | | 12/1998 |
| EP | 891758 | | 1/1999 |
| EP | 0893115 | | 1/1999 |
| EP | 0724418 | | 3/1999 |
| EP | 0725613 | | 3/1999 |
| EP | 0725616 | | 3/1999 |
| EP | 904755 | | 3/1999 |
| EP | 0916327 | | 5/1999 |
| EP | 925769 | A2 | 6/1999 |
| EP | 933074 | | 8/1999 |
| EP | 937736 | | 8/1999 |
| EP | 1 088 537 | A2 * | 9/1999 |
| EP | 941157 | | 9/1999 |
| EP | 947549 | | 10/1999 |
| EP | 951887 | B1 | 10/1999 |
| EP | 0951890 | | 10/1999 |
| EP | 2295493 | | 10/1999 |
| EP | 2305749 | | 10/1999 |
| EP | 2330152 | | 10/1999 |

(56) References Cited

FOREIGN PATENT DOCUMENTS

| | | |
|---|---|---|
| EP | 953326 | 11/1999 |
| EP | 0978263 A1 | 2/2000 |
| EP | 985397 B1 | 3/2000 |
| EP | 0778762 | 4/2000 |
| EP | 1005847 | 6/2000 |
| EP | 1008333 | 6/2000 |
| EP | 1013252 B1 | 6/2000 |
| EP | 1018999 | 7/2000 |
| EP | 1019002 B1 | 7/2000 |
| EP | 1019003 B1 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1 088 537 A2 | 4/2001 |
| EP | 0796068 | 5/2001 |
| EP | 1 116 479 A2 | 7/2001 |
| EP | 752892 | 7/2001 |
| EP | 0790839 | 8/2001 |
| EP | 1132069 | 9/2001 |
| EP | 1209271 A1 * | 12/2001 |
| EP | 1173128 | 1/2002 |
| EP | 1175194 B1 | 1/2002 |
| EP | 1184018 | 3/2002 |
| EP | 1192312 B1 | 4/2002 |
| EP | 1196122 B2 | 4/2002 |
| EP | 1199059 | 4/2002 |
| EP | 1199327 | 4/2002 |
| EP | 1208824 | 5/2002 |
| EP | 0793469 | 6/2002 |
| EP | 1210925 | 6/2002 |
| EP | 1224922 | 7/2002 |
| EP | 1225857 | 7/2002 |
| EP | 1253231 | 10/2002 |
| EP | 1262531 A1 | 12/2002 |
| EP | 1263374 B1 | 12/2002 |
| EP | 0737056 | 1/2003 |
| EP | 1275358 | 1/2003 |
| EP | 1275361 | 1/2003 |
| EP | 1293187 | 3/2003 |
| EP | 1304986 B1 | 5/2003 |
| EP | 1332742 B1 | 8/2003 |
| EP | 1339368 | 9/2003 |
| EP | 1374817 | 1/2004 |
| EP | 1388334 | 2/2004 |
| EP | 1402863 | 3/2004 |
| EP | 962208 | 8/2004 |
| EP | 1447066 | 8/2004 |
| EP | 1447067 | 8/2004 |
| EP | 1460987 | 9/2004 |
| EP | 963749 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 1586289 | 10/2005 |
| EP | 1588723 | 10/2005 |
| EP | 1605882 | 12/2005 |
| EP | 1609448 | 12/2005 |
| EP | 1621166 | 2/2006 |
| EP | 1621167 | 2/2006 |
| EP | 1632206 | 3/2006 |
| EP | 1642556 | 4/2006 |
| EP | 1403419 | 5/2006 |
| EP | 1656162 | 5/2006 |
| EP | 1669046 | 6/2006 |
| EP | 1688114 | 8/2006 |
| EP | 2314265 | 8/2006 |
| EP | 1723939 | 11/2006 |
| EP | 1738727 | 1/2007 |
| EP | 1754461 | 2/2007 |
| EP | 1787611 | 5/2007 |
| EP | 1813238 | 8/2007 |
| EP | 2008626 | 12/2008 |
| EP | 2055279 A1 | 5/2009 |
| EP | 2093049 | 8/2009 |
| EP | 2130522 | 12/2009 |
| EP | 1621165 | 4/2010 |
| EP | 2444046 | 4/2012 |
| EP | 2532328 | 12/2012 |
| EP | 2532329 A1 | 12/2012 |
| EP | 2532332 A1 | 12/2012 |
| EP | 2679210 A1 | 1/2014 |
| EP | 2740449 | 6/2014 |
| EP | 2740450 | 6/2014 |
| EP | 2740452 | 6/2014 |
| ES | 2213491 | 8/2004 |
| FR | 2566631 | 1/1986 |
| FR | 2583377 | 12/1986 |
| FR | 2612770 | 9/1988 |
| FR | 2810234 | 12/2001 |
| GB | 1333081 A | 8/1971 |
| GB | 1307441 | 2/1973 |
| GB | 1513055 | 6/1978 |
| GB | 2101468 | 1/1983 |
| GB | 2170108 | 7/1986 |
| GB | 2262873 | 7/1993 |
| GB | 2288540 A | 6/1994 |
| GB | 2354449 | 3/2001 |
| GB | 2452260 A | 10/2007 |
| GR | 851769 | 11/1985 |
| IN | 0984/KOL/1999 | 10/2005 |
| IN | 212479 B | 3/2007 |
| IN | 208543 B | 8/2007 |
| IN | 0980/MUM/2009 | 6/2009 |
| JP | 5572928 U | 5/1980 |
| JP | 598322 U | 1/1984 |
| JP | 630148323 U | 9/1988 |
| JP | 2107250 | 4/1990 |
| JP | 03224481 B2 | 10/1991 |
| JP | 04122256 | 4/1992 |
| JP | 04341368 | 11/1992 |
| JP | 06191505 | 7/1994 |
| JP | 06-269475 | 9/1994 |
| JP | 07124193 | 5/1995 |
| JP | 08215629 | 8/1996 |
| JP | H10295728 | 11/1998 |
| JP | 10328232 | 12/1998 |
| JP | 11033056 A | 2/1999 |
| JP | 11318980 | 11/1999 |
| JP | 11320742 | 11/1999 |
| JP | 2000232985 | 8/2000 |
| JP | 2000238161 | 9/2000 |
| JP | 2001037810 | 2/2001 |
| JP | 2001046435 A | 2/2001 |
| JP | 2001120597 | 5/2001 |
| JP | 2001158074 | 6/2001 |
| JP | 2001178768 A | 7/2001 |
| JP | 2001198157 | 7/2001 |
| JP | 2001224626 A | 8/2001 |
| JP | 2001277394 | 10/2001 |
| JP | 03420481 B2 | 11/2001 |
| JP | 2001321397 | 11/2001 |
| JP | 2001353174 A | 12/2001 |
| JP | 2002052042 A | 2/2002 |
| JP | 2002065718 | 3/2002 |
| JP | 2002-113800 | 4/2002 |
| JP | 2002165832 | 6/2002 |
| JP | 2002165836 | 6/2002 |
| JP | 2002178429 | 6/2002 |
| JP | 2002272769 A | 9/2002 |
| JP | 2002 325799 | 11/2002 |
| JP | 2002320641 | 11/2002 |
| JP | 2002325792 A | 11/2002 |
| JP | 2002369841 A | 12/2002 |
| JP | 2003126140 | 5/2003 |
| JP | 2003153955 A | 5/2003 |
| JP | 2003265523 | 9/2003 |
| JP | 2003265524 A | 9/2003 |
| JP | 2003275237 | 9/2003 |

(56) References Cited

FOREIGN PATENT DOCUMENTS

| | | |
|---|---|---|
| JP | 2003325563 | 11/2003 |
| JP | 2004089269 | 3/2004 |
| JP | 03566012 B2 | 6/2004 |
| JP | 03568146 B2 | 6/2004 |
| JP | 03616077 B2 | 11/2004 |
| JP | 2004337314 A | 12/2004 |
| JP | 2004337385 A | 12/2004 |
| JP | 2004350864 | 12/2004 |
| JP | 03640475 B2 | 1/2005 |
| JP | 2005000312 A | 1/2005 |
| JP | 03660816 B2 | 3/2005 |
| JP | 03676219 B2 | 5/2005 |
| JP | 03688403 B2 | 6/2005 |
| JP | 03705943 B2 | 8/2005 |
| JP | 03719819 B2 | 9/2005 |
| JP | 03724963 B2 | 9/2005 |
| JP | 03725008 B2 | 9/2005 |
| JP | 03737376 B2 | 11/2005 |
| JP | 2006014792 A | 1/2006 |
| JP | 03781617 B2 | 3/2006 |
| JP | 2006110329 | 4/2006 |
| JP | 2006513824 T | 4/2006 |
| JP | 03801449 B2 | 5/2006 |
| JP | 2006116036 A | 5/2006 |
| JP | 03850102 B2 | 9/2006 |
| JP | 03850207 B2 | 9/2006 |
| JP | 03856941 B2 | 9/2006 |
| JP | 03868628 B2 | 10/2006 |
| JP | 03874499 B2 | 11/2006 |
| JP | 03877702 B2 | 11/2006 |
| JP | 2006325639 A | 12/2006 |
| JP | 2006346021 | 12/2006 |
| JP | 03904356 B2 | 1/2007 |
| JP | 2007007455 A | 1/2007 |
| JP | 2007007456 A | 1/2007 |
| JP | 03926042 B2 | 3/2007 |
| JP | 03934855 B2 | 3/2007 |
| JP | 2007089906 A | 4/2007 |
| JP | 2007105198 A | 4/2007 |
| JP | 2007152033 A | 6/2007 |
| JP | 03986210 B2 | 7/2007 |
| JP | 03986222 B2 | 7/2007 |
| JP | 2007167453 | 7/2007 |
| JP | 2007175515 A | 7/2007 |
| JP | 2007195665 A | 8/2007 |
| JP | 2007267763 A | 10/2007 |
| JP | 2007275491 A | 10/2007 |
| JP | 04035341 B2 | 11/2007 |
| JP | 04058281 B2 | 12/2007 |
| JP | 04061086 B2 | 12/2007 |
| JP | 04092319 B2 | 3/2008 |
| JP | 2008080150 A | 4/2008 |
| JP | 2008093289 A | 4/2008 |
| JP | 04124322 B2 | 5/2008 |
| JP | 2008119081 A | 5/2008 |
| JP | 2008136739 A | 6/2008 |
| JP | 2008136877 A | 6/2008 |
| JP | 04148594 B2 | 7/2008 |
| JP | 04148620 B2 | 7/2008 |
| JP | 2008154606 A | 7/2008 |
| JP | 04162609 B2 | 8/2008 |
| JP | 04162637 B2 | 8/2008 |
| JP | 04166923 B2 | 8/2008 |
| JP | 04167406 B2 | 8/2008 |
| JP | 04173723 B2 | 8/2008 |
| JP | 04190675 B2 | 9/2008 |
| JP | 04190693 B2 | 9/2008 |
| JP | 04208338 B2 | 10/2008 |
| JP | 2008246089 | 10/2008 |
| JP | 4177770 B2 | 11/2008 |
| JP | 04230971 B2 | 12/2008 |
| JP | 2008295475 A | 12/2008 |
| JP | 2008295713 A | 12/2008 |
| JP | 04261593 B2 | 2/2009 |
| JP | 2009112590 | 5/2009 |
| JP | 04322228 B2 | 6/2009 |
| JP | 2009136601 | 6/2009 |
| JP | 2009142401 A | 7/2009 |
| JP | 2009201878 A | 9/2009 |
| JP | 04392936 B2 | 10/2009 |
| JP | 2009232987 A | 10/2009 |
| JP | 2009261777 A | 11/2009 |
| JP | 2009291473 A | 12/2009 |
| JP | 2009297048 A | 12/2009 |
| JP | 2010017342 | 1/2010 |
| JP | 04458702 B2 | 2/2010 |
| JP | 04459013 B2 | 2/2010 |
| JP | 2010022560 | 2/2010 |
| JP | 04481325 B2 | 3/2010 |
| JP | 2010051654 A | 3/2010 |
| JP | 2010063814 A | 3/2010 |
| JP | 2010063944 A | 3/2010 |
| JP | 04492957 B2 | 4/2010 |
| JP | 2010068954 A | 4/2010 |
| JP | 2010075462 A | 4/2010 |
| JP | 2010082059 A | 4/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 | 6/2010 |
| JP | 2010131297 A | 6/2010 |
| JP | 2010136917 A | 6/2010 |
| JP | 2010136973 A | 6/2010 |
| JP | 04540563 B2 | 7/2010 |
| JP | 04587947 B2 | 9/2010 |
| JP | 2010194124 A | 9/2010 |
| JP | 2010201093 | 9/2010 |
| JP | 2010221067 | 10/2010 |
| JP | 4577766 B2 | 11/2010 |
| JP | 04620299 B2 | 11/2010 |
| JP | 04627472 B2 | 11/2010 |
| JP | 04627473 B2 | 11/2010 |
| JP | 04638087 B2 | 12/2010 |
| JP | 04652626 B2 | 12/2010 |
| JP | 2010273842 A | 12/2010 |
| JP | 2010284418 A | 12/2010 |
| JP | 2011000480 A | 1/2011 |
| JP | 2011030700 | 2/2011 |
| JP | 04693574 B2 | 3/2011 |
| JP | 2011067484 A | 4/2011 |
| JP | 2011072720 A | 4/2011 |
| JP | 2011104014 | 6/2011 |
| JP | 2011104122 A | 6/2011 |
| JP | 2011120661 A | 6/2011 |
| JP | 2011125360 A | 6/2011 |
| JP | 2011125537 | 6/2011 |
| JP | 04776516 B2 | 7/2011 |
| JP | 2011130797 A | 7/2011 |
| JP | 2011130799 A | 7/2011 |
| JP | 2011156032 A | 8/2011 |
| JP | 2011156070 A | 8/2011 |
| JP | 2011156254 | 8/2011 |
| JP | 04824882 B2 | 9/2011 |
| JP | 4850272 B2 | 10/2011 |
| JP | 04855533 B2 | 11/2011 |
| JP | 2011239858 | 12/2011 |
| JP | 04931572 B2 | 2/2012 |
| JP | 04937225 B2 | 3/2012 |
| JP | 04953618 B2 | 3/2012 |
| JP | 04969437 B2 | 4/2012 |
| JP | 04969640 B2 | 4/2012 |
| JP | 4971491 B2 | 4/2012 |
| JP | 04974524 B2 | 4/2012 |
| JP | 04979780 B2 | 4/2012 |
| JP | 05016020 B2 | 6/2012 |
| JP | 05027364 B2 | 6/2012 |
| JP | 2012115378 | 6/2012 |
| JP | 05031082 B2 | 7/2012 |
| JP | 05042351 B2 | 7/2012 |

(56) References Cited

FOREIGN PATENT DOCUMENTS

| | | |
|---|---|---|
| JP | 05043569 B2 | 7/2012 |
| JP | 05043591 B2 | 7/2012 |
| JP | 05046488 B2 | 7/2012 |
| JP | 2012125452 | 7/2012 |
| JP | 2012125625 A | 7/2012 |
| JP | 05053765 B2 | 8/2012 |
| JP | 05070275 B2 | 8/2012 |
| JP | 05079931 B1 | 9/2012 |
| JP | 05080189 B2 | 9/2012 |
| JP | 05084442 B2 | 9/2012 |
| JP | 05084476 B2 | 9/2012 |
| JP | 5085770 B2 | 9/2012 |
| JP | 05089269 B2 | 9/2012 |
| JP | 2012179286 | 9/2012 |
| JP | 05113146 B2 | 10/2012 |
| JP | 05129536 B2 | 11/2012 |
| JP | 05105884 B2 | 12/2012 |
| JP | 5715806 B2 | 5/2015 |
| KR | 20010005620 | 1/2001 |
| KR | 20020035634 | 5/2002 |
| KR | 20080028771 | 4/2008 |
| SE | 9400916 | 3/1994 |
| SE | 9704893 | 12/1997 |
| WO | WO9015830 | 12/1990 |
| WO | WO9219198 | 11/1992 |
| WO | WO9321237 | 10/1993 |
| WO | WO9321879 | 11/1993 |
| WO | WO9510996 | 4/1995 |
| WO | WO9511652 | 5/1995 |
| WO | WO 1995/016746 A1 | 6/1995 |
| WO | WO9514453 | 6/1995 |
| WO | WO9515139 | 6/1995 |
| WO | WO9516424 | 6/1995 |
| WO | WO9519753 | 7/1995 |
| WO | WO9521596 | 8/1995 |
| WO | WO9524173 | 9/1995 |
| WO | WO9526209 | 10/1995 |
| WO | WO9529657 | 11/1995 |
| WO | WO9532698 | 12/1995 |
| WO | WO9534329 | 12/1995 |
| WO | WO 96/19173 A1 | 6/1996 |
| WO | WO9616624 | 6/1996 |
| WO | WO96029967 | 10/1996 |
| WO | WO 97/11659 | 4/1997 |
| WO | WO9717922 | 5/1997 |
| WO | WO 9724096 | 7/1997 |
| WO | WO9816179 | 4/1998 |
| WO | WO9816180 | 4/1998 |
| WO | WO9843684 | 10/1998 |
| WO | WO9913813 | 3/1999 |
| WO | WO9934841 | 7/1999 |
| WO | WO9951178 | 10/1999 |
| WO | WO200000235 | 1/2000 |
| WO | WO200032145 | 6/2000 |
| WO | WO200059430 | 10/2000 |
| WO | WO 01/15647 | 3/2001 |
| WO | WO200126596 | 4/2001 |
| WO | WO 0135886 | 5/2001 |
| WO | WO200207663 | 1/2002 |
| WO | WO200232962 | 4/2002 |
| WO | WO 2002/064877 A2 | 8/2002 |
| WO | WO2002067809 | 9/2002 |
| WO | WO2003009794 | 2/2003 |
| WO | WO2003039402 | 5/2003 |
| WO | WO2003053297 | 7/2003 |
| WO | WO03079946 | 10/2003 |
| WO | WO03101622 | 12/2003 |
| WO | WO2003105738 | 12/2003 |
| WO | WO2004021946 | 3/2004 |
| WO | WO2004049995 | 6/2004 |
| WO | WO 2004/071539 A3 | 8/2004 |
| WO | WO2004084784 | 10/2004 |
| WO | WO2004105664 | 12/2004 |
| WO | WO2005/018694 | 3/2005 |
| WO | WO2005087164 | 9/2005 |
| WO | WO 2005/102237 | 11/2005 |
| WO | WO2006104024 | 5/2006 |
| WO | WO 2006/062258 A2 | 6/2006 |
| WO | WO2006059922 | 6/2006 |
| WO | WO2006066029 | 6/2006 |
| WO | WO2006083584 | 8/2006 |
| WO | WO2006134904 | 12/2006 |
| WO | WO2006134906 | 12/2006 |
| WO | WO2007000315 | 1/2007 |
| WO | WO2007046052 | 4/2007 |
| WO | WO2007047598 | 4/2007 |
| WO | WO2007049725 | 5/2007 |
| WO | WO2007061035 | 5/2007 |
| WO | WO 2007/141744 | 12/2007 |
| WO | WO2007142145 | 12/2007 |
| WO | WO2007148502 | 12/2007 |
| WO | WO2008018922 | 2/2008 |
| WO | WO2008065945 | 6/2008 |
| WO | WO2008146749 | 12/2008 |
| WO | WO2008155699 | 12/2008 |
| WO | WO2009004941 | 1/2009 |
| WO | WO2009005431 | 1/2009 |
| WO | WO2009139248 | 1/2009 |
| WO | WO2009139255 | 1/2009 |
| WO | WO2009041223 | 4/2009 |
| WO | WO2009096108 | 8/2009 |
| WO | WO2009107435 | 9/2009 |
| WO | WO2009122830 | 10/2009 |
| WO | WO2009152018 | 12/2009 |
| WO | WO2009155264 | 12/2009 |
| WO | WO2009155265 | 12/2009 |
| WO | WO2010071508 | 6/2010 |
| WO | WO2010074319 | 7/2010 |
| WO | WO2010107096 | 9/2010 |
| WO | WO2010114052 | 10/2010 |
| WO | WO2010117015 | 10/2010 |
| WO | WO2010118272 | 10/2010 |
| WO | WO201153044 | 5/2011 |
| WO | WO2011118725 | 9/2011 |
| WO | WO2011118842 | 9/2011 |
| WO | WO2011145653 | 11/2011 |
| WO | WO2011150955 | 12/2011 |
| WO | WO2011163582 | 12/2011 |
| WO | WO2012002252 | 1/2012 |
| WO | WO2012014436 | 2/2012 |
| WO | WO2012042908 | 4/2012 |
| WO | WO2012043077 | 4/2012 |
| WO | WO2012043078 | 4/2012 |
| WO | WO2012052172 | 4/2012 |
| WO | WO2012043082 | 5/2012 |
| WO | WO2012067216 | 5/2012 |
| WO | WO2012073499 | 6/2012 |
| WO | WO2012074466 | 6/2012 |
| WO | WO201291016 | 7/2012 |
| WO | WO2012090508 | 7/2012 |
| WO | WO2012101934 | 8/2012 |
| WO | WO2012102034 | 8/2012 |
| WO | WO 2012117764 | 9/2012 |
| WO | WO2012117824 | 9/2012 |
| WO | WO2012132460 | 10/2012 |
| WO | WO 2012/177400 | 12/2012 |
| WO | WO2012170778 | 12/2012 |
| WO | WO2012170779 | 12/2012 |
| WO | WO2012170781 | 12/2012 |
| WO | WO2012170808 | 12/2012 |
| WO | WO2012174026 | 12/2012 |
| WO | WO2013001788 | 1/2013 |
| WO | WO2013046701 | 4/2013 |
| WO | WO2013060733 | 5/2013 |
| WO | WO2014073636 | 5/2014 |
| WO | WO2014078247 | 5/2014 |

OTHER PUBLICATIONS

All Office Actions, U.S. Appl. No. 10/776,839.
All Office Actions, U.S. Appl. No. 11/717,235.
All Office Actions, U.S. Appl. No. 10/717,556.
All Office Actions, U.S. Appl. No. 10/717,234.

(56) References Cited

OTHER PUBLICATIONS

All Office Actions, U.S. Appl. No. 11/973,811.

\* cited by examiner

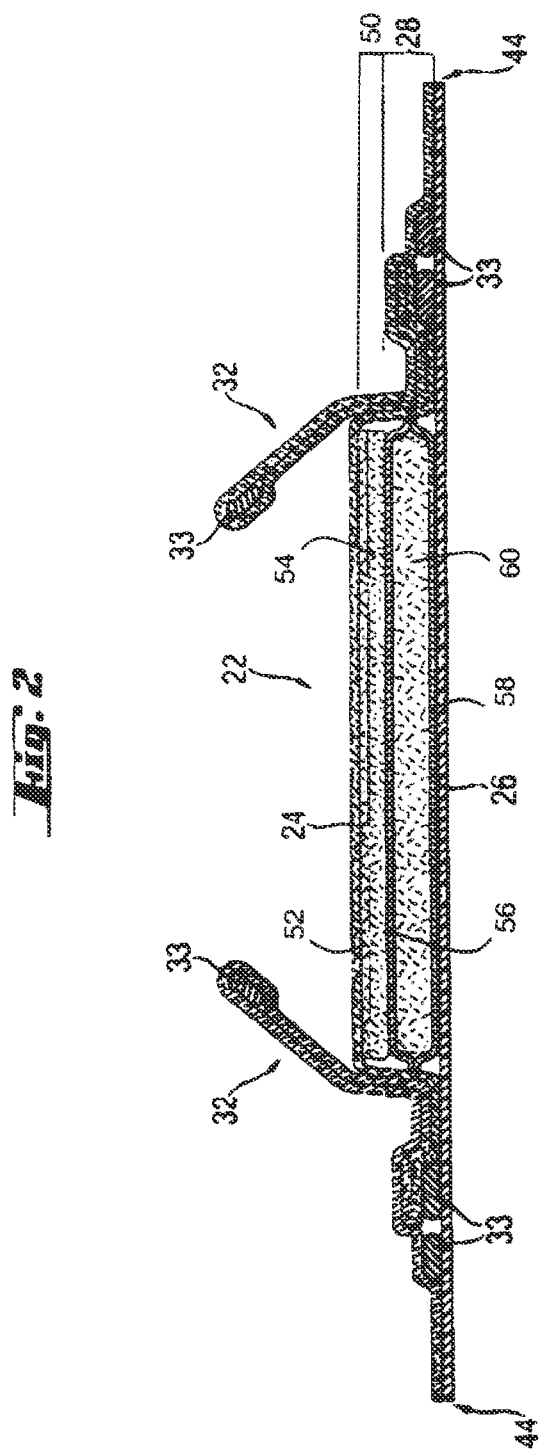

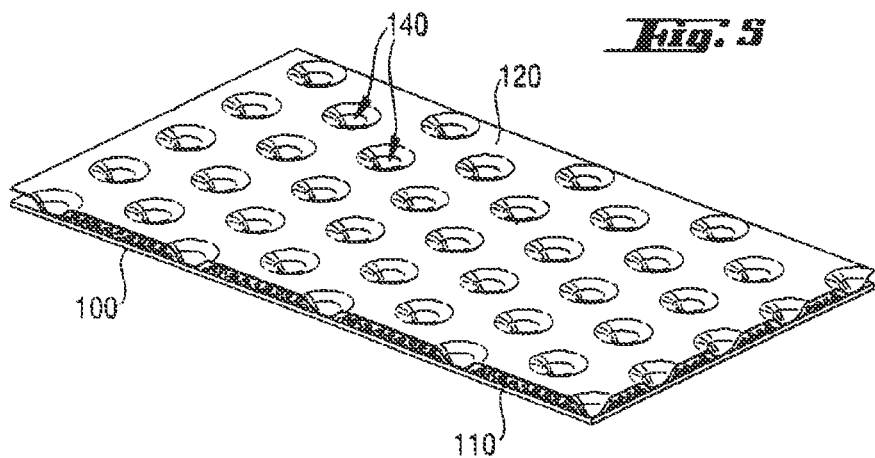
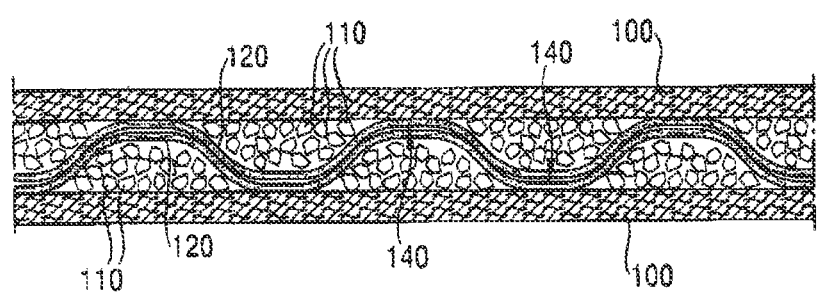

THIN AND DRY DIAPER

FIELD OF THE INVENTION

The present invention concerns an absorbent article, preferably a disposable absorbent article, such as a diaper. The present invention specifically concerns an absorbent core for such an absorbent article that provides an improved immobilization of absorbent polymer material when the article is fully or partially urine loaded. This absorbent core is useful for providing an absorbent article of increased wearing comfort, which is thin and dry.

BACKGROUND

Absorbent articles, such as diapers and adult incontinence products are well known articles of staple manufacturing. Multiple attempts have been made to provide them with an overall good fit and with a high absorbent capacity. Modern diapers make use of absorbent polymer materials or so-called superabsorbent materials, which allow for storage of amounts of liquid as high as 300 ml of in a typical baby diaper.

While such a diaper is generally a disposable product it is in some instances worn over many hours and worn in a dry state as well as in a urine loaded state.

Hence, to provide good wearing comfort it is very important to keep the absorbent materials of a diaper or other absorbent article in their intended position, both when the article is dry and when the article is fully or partially loaded with urine (or other bodily liquids).

U.S. Pat. No. 4,381,783 (Elias) discloses an absorbent article with a core comprising pockets of absorbent hydrocolloid material. These pockets are provided as to confine the movement of the hydrocolloid material, in particular when the article is fully or partially loaded with urine. The pockets form part of an absorbent layer and are typically provided from cellulose material. Hence, to achieve good immobilization of the hydrocolloid material according to the teaching of this patent, a relatively high amount of cellulosic material is required. Moreover, the provision of such pockets may hinder the free distribution of liquid to the more absorbent areas of the core, for example the areas of hydrocolloid materials.

U.S. Pat. No. 5,944,706 (Palumbo) discloses an absorbent structure comprising two fibre layers and an intermediate layer. This intermediate layer comprises an absorbent hydrogel material in an amount exceeding 120 g/m$^2$ and particles of an thermoplastic material. While this construction certainly provides good immobilisation of the absorbent hydrogel particles in the dry state, it seems that only a lesser immobilisation can be achieved in the urine loaded state. The disclosed thermoplastic materials appear to swell much less than the disclosed hydrogel materials. Therefore, in particular when the absorbent structure is to be used in a product to absorb high amounts of liquids, for example a diaper, the wet immobilisation may not be fully satisfactory.

U.S. Pat. No. 5,411,497 (Tanzer) discloses an absorbent article which includes superabsorbent material located in discrete pockets. The absorbent article comprises a first and a second carrier layer and water-sensitive attaching means for securing together the carrier layers and to provide a plurality of pocket regions. The article comprises high-absorbency material located within said pocket regions. The water-sensitive attachment means provides a wet strength which is less than a separating force imparted by a swelling of that high-absorbency material when that high-absorbency material is exposed to an aqueous liquid. The absorbent article is said to provide an absorbent structure which more securely locates and contains the high-absorbency material in a selected way of pockets when the article is dry. However, due to the construction of the pockets, and specifically due to the selection of the water-sensitive attachment means, these pockets are not maintained when the article is fully or partially loaded with liquids. Therefore, it is believed that this absorbent article does not provide a very satisfactory immobilization of the absorbent material in the fully or partially urine loaded state.

SUMMARY

The present invention concerns an absorbent article, preferably a disposable absorbent article, such as a diaper. An absorbent core useful for an absorbent article is disclosed which imparts increased wearing comfort to the article and makes it thin and dry. Further disclosed is a process for obtaining such a core. Specifically disclosed is an absorbent core useful for an absorbent article comprising a substrate layer, the substrate layer comprising a first surface and a second surface, the absorbent core further comprising a discontinuous layer of absorbent material, the absorbent material comprising an absorbent polymer material, the absorbent material optionally comprising an absorbent fibrous material and the absorbent fibrous material not representing more than 20 weight percent of the total weight of the absorbent polymer material, the discontinuous layer of absorbent material comprising a first surface and a second surface, the absorbent core further comprising a layer of thermoplastic material, the layer of thermoplastic material comprising a first surface and a second surface and wherein the second surface of the discontinuous layer of absorbent material is in at least partial contact with the first surface of the subject layer and wherein portions of the second surface of the layer of thermoplastic material are in direct contact with the first surface of the substrate layer and portions of the second surface of the layer of thermoplastic material are in direct contact with the first surface of the discontinuous layer of absorbent material.

Further disclosed is a process for providing a storage layer for an absorbent core useful in an absorbent article, the process comprising the steps of:

providing a substrate material comprising a first surface and a second surface depositing absorbent material onto the first surface of the substrate material in a pattern, the pattern comprising at least one zone which is substantially free of absorbent material, and the pattern comprising at least one zone comprising absorbent material depositing a thermoplastic material onto the first surface of the substrate material and the absorbent material, such that portions of the thermoplastic material are in direct contact with the first surface of the substrate and portions of the thermoplastic material are in direct contact with the absorbent material.

BRIEF DESCRIPTION OF THE DRAWINGS

FIG. 5 is a perspective view of a preferred embodiment of the absorbent core.

FIG. 6 is a cross-sectional view of a preferred embodiment of the absorbent core.

FIG. 7 is a schematic representation of the rheometer

DETAILED DESCRIPTION

The present invention concerns an absorbent article, preferably a disposable absorbent article, such as a diaper.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Diaper" refers to an absorbent article generally worn by infants and incontinent persons about the lower torso.

"Comprise," "comprising," and "comprises" is an open ended term that specifies the presence of what follows, e.g., a component but does not preclude the presents of other features, elements, steps or components known in the art, or disclosed herein.

Figure 1:
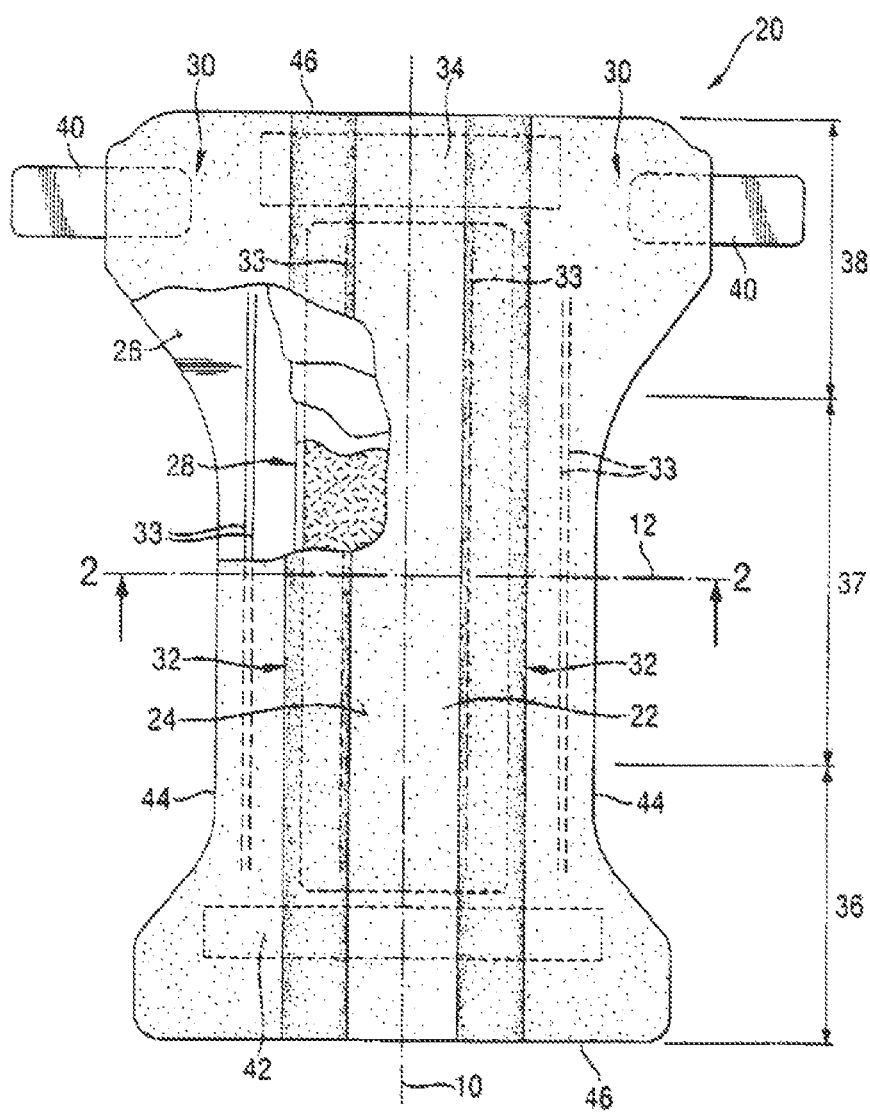
FIG. 1 is a plan view of a diaper as a preferred embodiment of an absorbent article according to the present invention.

FIG. 1 is a plan view of a diaper 20 as a preferred embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis may include a portion of an absorbent core 28 encased between the topsheet 24 and the backsheet 26. The chassis may also include most or all of the absorbent core 28 encased between the topsheet 24 and the backsheet 26. The chassis preferably further includes side panels 30, elasticized leg cuffs 32, and elastic waist feature 34, the leg cuffs 32 and the elastic waist feature each typically comprise elastic members 33. One end portion of the diaper 20 is configured as a first waist region 36 of the diaper 20. The opposite end portion is configured as a second waist region 38 of the diaper 20. An intermediate portion of the diaper 20 is configured as a crotch region 37, which extends longitudinally between the first and second waist regions 36 and 38. The waist regions 36 and 38 may include elastic elements such that they gather about the waist of the wearer to provide improved fit and containment (elastic waist feature 34). The crotch region 37 is that portion of the diaper 20 which, when the diaper 20 is worn, is generally positioned between the wearer's legs. The diaper 20 is depicted with its longitudinal axis 10 and its transverse axis 12. The periphery of the diaper 20 is defined by the outer edges of the diaper 20 in which the longitudinal edges 44 run generally parallel to the longitudinal axis 100 of the diaper 20 and the end edges 46 run between the longitudinal edges 44 generally parallel to the transverse axis 110 of the diaper 20. The chassis also comprises a fastening system, which may include at least one fastening member 40 and at least one stored landing zone 42.

For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 24 in FIG. 1 may be fully or partially elasticized or may be foreshortened to provide a void space between the topsheet 24 and the absorbent core 28. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. The absorbent core 28 may further comprise minor amounts (typically less than 10%) of non-liquid absorbent materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

The backsheet 26 may be joined with the topsheet 24. The backsheet 26 prevents the exudates absorbed by the absorbent core 28 and contained within the article 20 from soiling other external articles that may contact the diaper 20, such as bed sheets and undergarments. In preferred embodiments, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

The diaper 20 may also include such other features as are known in the art including front and rear ear panels, waist cap features, elastics and the like to provide better fit, containment and aesthetic characteristics. Such additional features are well known in the art and are e.g., described in U.S. Pat. Nos. 3,860,003 and 5,151,092.

In order to keep the diaper 20 in place about the wearer, preferably at least a portion of the first waist region 36 is attached by the fastening member 42 to at least a portion of the second waist region 38, preferably to form leg opening (s) and an article waist. When fastened, the fastening system carries a tensile load around the article waist. The fastening system is designed to allow an article user to hold one element of the fastening system such as the fastening member 42, and connect the first waist region 36 to the second waist region 38 in at least two places. This is achieved through manipulation of bond strengths between the fastening device elements.

Diapers 20 according to the present invention may be provided with a re-closable fastening system or may alternatively provided in the form of pant-type diapers.

The fastening system and any component thereof may include any material suitable for such a use, including but not limited to plastics, films, foams, nonwoven webs, woven webs, paper, laminates, fiber reinforced plastics and the like, or combinations thereof. It may be preferable that the materials making up the fastening device be flexible. The flexibility is designed to allow the fastening system to conform to the shape of the body and thus, reduces the likelihood that the fastening system will irritate or injure the wearer's skin.

Figure 2:
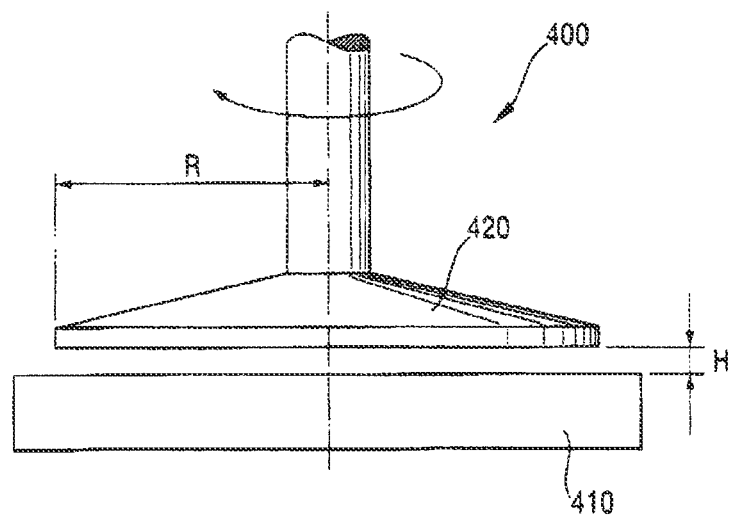
FIG. 2 is a cross-sectional view of the diaper shown in FIG. 1 taken along the sectional line 2-2 of FIG. 1.

FIG. 2 shows a cross section of FIG. 1 taken along the sectional line 2-2 of FIG. 1. Starting from the wearer facing side the diaper comprises the topsheet 24, the components of the absorbent core 28, and the backsheet 26. The absorbent article preferably comprises an acquisition system 50, which comprises an upper acquisition layer 52 facing towards the wearer's skin and a lower acquisition 54 layer facing the garment of the wearer. In one preferred embodiment the upper acquisition layer 52 comprises a non-woven whereas the lower acquisition layer preferably comprises a mixture of chemically stiffened, twisted and curled fibers, high surface area fibers and thermoplastic binding fibers. In another preferred embodiment both acquisition layers are provided from a non-woven material, which is preferably hydrophilic. The acquisition layer preferably may be in direct contact with the storage layer 60.

The storage layer 60 may be wrapped by a core wrap material. In one preferred embodiment the core wrap material comprises a top layer 56 and a bottom layer 58. The core wrap material, the top layer 56 or the bottom layer 58 can be provided from a non-woven material. One preferred material is a so called SMS material, comprising a spunbonded, a melt-blown and a further spunbonded layer. Highly preferred are permanently hydrophilic non-wovens, and in particular nonwovens with durably hydrophilic coatings. An alternative preferred material comprises a SMMS-structure.

The top layer 56 and the bottom layer 58 may be provided from two or more separate sheets of materials or they may be alternatively provided from a unitary sheet of material. Such a unitary sheet of material may be wrapped around the storage layer 60 e.g., in a C-fold.

Preferred non-woven materials are provided from synthetic fibers, such as PE, PET and most preferably PP. As the polymers used for nonwoven production are inherently hydrophobic, they are preferably coated with hydrophilic coatings.

A preferred way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. patent application Ser. No. 10/674,670.

An alternative preferred way to produce nonwovens with durably hydrophilic coatings is to coat the nonwoven with hydrophilic nanoparticles as described in co-pending application Ser. No. 10/060,708 and WO 02/064877.

Typically, nanoparticles have a largest dimension of below 750 nm. Nanoparticles with sizes ranging form 2 to 750 nm can be economically produced. The advantages of nanoparticles is that many of them can be easily dispersed in water solution to enable coating application onto the nonwoven; they typically form transparent coatings, and the coatings applied from water solutions are typically sufficiently durable to exposure to water.

Nanoparticles can be organic or inorganic, synthetic or natural. Inorganic nanoparticles generally exist as oxides, silicates, carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.)

A highly preferred nanoparticle coated non-woven is disclosed in the co-pending patent application Ser. No. 10/758,066 entitled "Disposable absorbent article comprising a durable hydrophilic core wrap" to the inventors Ekaterina Anatolyevna Ponomarenko and Mattias NMN Schmidt.

Further useful non-wovens are described in U.S. Pat. No. 6,645,569 to Cramer et al. and co-pending patent application Ser. No. 10/060,694 to Cramer et al., Ser. No. 10/060,708 to Rohrbaugh et al., Ser. No. 10/338,603 to Cramer et al., and Ser. No. 10/338,610 to Cramer et al.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic non-wovens are also useful in other parts of an absorbent article. For example, topsheets and acquisition layers comprising permanently hydrophilic non-wovens as described above have been found to work well.

In summary, in one aspect of the present invention, absorbent articles are preferred which comprise a nonwoven fabric, the nonwoven fabric comprising a plurality of fibers and having a surface tension of at least 55, preferably at least 60 and most preferably at least 65 mN/m or higher when being wetted with saline solution and has a liquid strike through time of less than 5 s for a fifth gush of liquid.

The surface tension is a measure of how permanently a certain hydrophilicity level is achieved. The value is to be measured using the test method described hereinbelow.

The liquid strike through time is a measure of a certain hydrophilicity level. The value is to be measured using the test method described hereinbelow.

In a preferred embodiment of the present invention the absorbent core 28 comprises a substrate layer 100, absorbent polymer material 110 and a fibrous layer of adhesive 120. The substrate layer 100 is preferably provided from a non-woven material, preferred non-wovens are those exemplified above for the top layer 56 or the bottom layer 58.

The substrate layer 100 comprises a first surface and a second surface. At least portions of the first surface of the substrate layer 100 are in direct contact with a layer of absorbent polymer material 110. This layer of absorbent polymer material 110 is preferably a discontinuous layer, and comprises a first surface and a second surface. As used herein, a discontinuous layer is a layer comprising openings. Typically these openings have a diameter or largest span of less than 10 mm, preferably less than 5 mm, 3 mm, 2 mm and of more than 0.5 mm, 1 mm or 1.5 mm. At least portions of the second surface of the absorbent polymer material layer 110 are in contact with at least portions of the first surface of the substrate layer material 100. The first surface of the absorbent polymer material 110 defines a certain height 112 of the layer of absorbent polymer above the first surface of the layer of substrate material 100. When the absorbent polymer material layer 110 is provided as a discontinuous layer, portions of the first surface of the substrate layer 100 are not covered by absorbent polymer material 110. The absorbent core 28 further comprises a thermoplastic composition 120. This thermoplastic composition 120 serves to at least partially immobilize the absorbent polymer material 110.

Figure 3:
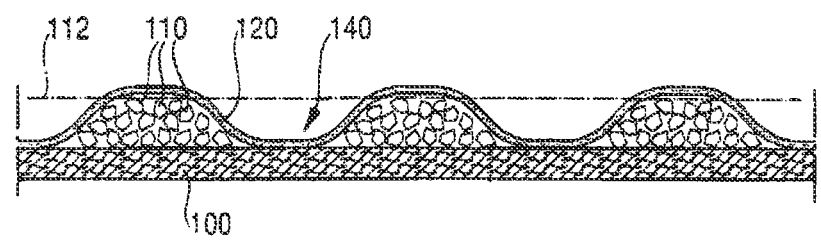
FIG. 3 is a cross-sectional view of a preferred embodiment of the absorbent core.

However, in an even more preferred embodiment of the present invention the thermoplastic material 120 is provided as a fibrous layer which is partially in contact with the absorbent polymer material 110 and partially in contact with the substrate layer 100. FIG. 3 shows such a preferred structure. In this preferred structure the absorbent polymer material layer 110 is provided as a discontinuous layer, a layer of fibrous thermoplastic material 120 is laid down onto the layer of absorbent polymeric material 110, such that the thermoplastic layer 120 is in direct contact with the first surface of the layer of absorbent polymer material 110, but also in direct contact with the first surface of the substrate layer 100, where the substrate layer is not covered by the absorbent polymeric material 110. This imparts an essentially three-dimensional structure to the fibrous layer of thermoplastic material 120 which in itself is essentially a two-dimensional structure of relatively small thickness (in z-direction), as compared to the extension in x- and y-direction. In other words, the fibrous thermoplastic material layer 120 undulates between the first surface of the absorbent polymer material 110 and the first surface of the substrate layer 100.

Thereby, the thermoplastic material 120 provides cavities to hold the absorbent polymer material 110, and thereby immobilizes this material. In a further aspect, the thermoplastic material 120 bonds to the substrate 100 and thus affixes the absorbent polymer material 110 to the substrate 100. Highly preferred thermoplastic materials will also penetrate into both the absorbent polymer material 110 and the substrate layer 100, thus providing for further immobilization and affixation.

Of course, while the thermoplastic materials disclosed herein provide a much improved wet immobilisation (i.e., immobilisation of absorbent material when the article is wet or at least partially loaded), these thermoplastic materials also provide a very good immobilisation of absorbent material when the article is dry.

In accordance with the present invention, the absorbent polymer material 110 may also be mixed with fibrous material, such as airfelt material, which can provide a matrix for further immobilization of the super-absorbent polymer material. However, preferably a relatively low amount of fibrous cellulose material is used, preferably less than 40 weight %, 20 or 10 weight % of cellulose fibrous material as compared to the weight of absorbent polymer material 110.

Figure 4:
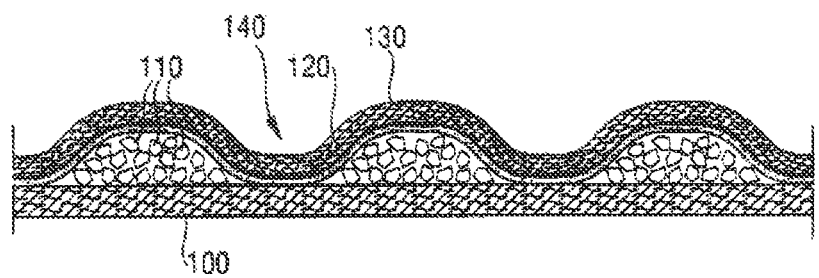
FIG. 4 is a cross-sectional view of a preferred embodiment of the absorbent core.

An alternative preferred embodiment of the present invention is shown in FIG. 4. The absorbent core shown in FIG. 4 further comprises a cover layer 130. This cover layer may be provided of the same material as the substrate layer 100, or may be provided from a different material. Preferred materials for the cover layer are the non-woven materials, typically the materials described above as useful for the top layer 56 and the bottom layer 58. In this embodiment portions of the cover layer 130 bond to portions of the substrate layer 100 via the thermoplastic material 120. Thereby, the substrate layer 100 together with the cover layer 130 provides cavities to immobilize the absorbent polymer material 110.

With reference to FIGS. 3 and 4 the areas of direct contact between the thermoplastic material 120 and the substrate material 100 are referred to as areas of junction 140. The shape number and disposition of the areas of junction 140 will influence the immobilization of the absorbent polymer material 110. The areas of junction can be of squared, rectangular or circular shape. Preferred areas of junction are of circular shape. Preferably, they have a diameter of more than 0.5 mm, or 1 mm, or 1.5 mm and of less than 10 mm, or 5 mm, or 3 mm, or 2 mm. If the areas of junction 140 are not of circular shape, they preferably are of a size as to fit inside a circle of any of the preferred diameters given above.

The areas of junction 140 can be disposed in a regular or irregular pattern. For example, the areas of junction 140 may be disposed along lines as shown in FIG. 5. These lines may be aligned with the longitudinal axis of the absorbent core, or alternatively they may have a certain angle in respect to the longitudinal edges of the core. It has been found, that a disposition along lines parallel with the longitudinal edges of the absorbent core 28 create channels in the longitudinal direction which lead to a lesser wet immobilization. Preferably, therefore the areas of junction 140 are arranged along lines which form an angle of 20 degree, 30 degree, 40 degree, or 45 degree with the longitudinal edges of the absorbent core 28. Another preferred pattern for the areas of junction 140 is a pattern comprising polygons, for example pentagons and hexagons or a combination of pentagons and hexagons. Also preferred are irregular patterns of areas of junction 140, which also have been found to give a good wet immobilization.

Two fundamentally different patterns of areas of junctions 140 can be chosen in accordance with the present invention. In one embodiment the areas of junctions are discrete. They are positioned within the areas of absorbent material, like islands in a sea. The areas of absorbent materials are then referred to as connected areas. In an alternative embodiment, the areas of junctions can be connected. Then, the absorbent material can be deposited in a discrete pattern, or in other words the absorbent material represents islands in a sea of thermoplastic material 120. Hence, a discontinuous layer of absorbent polymer material 110 may comprise connected areas of absorbent polymer material 110 or may comprise discrete areas of absorbent polymer material 110.

In a further aspect of the present invention, it has been found that absorbent cores providing for a good wet immobilization can be formed by combining two layers as shown in FIG. 3 and as described in the context thereof. Such an embodiment is shown in FIG. 6. The absorbent core material shown in FIG. 6 comprises two substrate layers 100, two layers of absorbent polymer material 110 and two layers of fibrous thermoplastic materials 120. When two discontinuous layers of an absorbent polymer material 110 are used, they would be typically arranged in such a way that the absorbent polymer material of the one layer faces the areas of junction 140 of the other layer. In an alternative preferred embodiment, however, the areas of junction 140 are offset and do not face each other. Hence preferably, when two storage layers are joined, this is done such that the first surface of the substrate layer 100 of the first storage layer 60 faces the first surface of the substrate layer 100 of the second storage layer 60.

The present invention, and specifically the preferred embodiment described with reference to FIGS. 3, 4 and 6 can be used to provide the storage layer 60 of an absorbent core. However, they can also be used to provide the full absorbent core 28. In that case, no further materials wrapping the core, such as the top layer 56 and the bottom layer 58 are being used. With reference to the embodiment of FIG. 3 the substrate layer 100 may provide the function of the bottom layer 58 and the layer of fibrous thermoplastic material 120 may provide the function of the top layer 56. With reference to FIG. 4 the cover layer 130 may provide the function of the top layer 56 and the substrate layer 100 may provide the function of the bottom layer 58. With reference to FIG. 6, the two substrate layers 100 used may provide the functions of the top layer 56 and the bottom layer 58, respectively.

According to the present invention the thermoplastic layer 120 can comprise any thermoplastic composition, preferred are adhesive thermoplastic compositions, also referred to as hot melt adhesives. A variety of thermoplastic compositions are suitable to immobilize absorbent material.

Some initially thermoplastic materials may later lose their thermoplasticity due to a curing step, e.g., initiated via heat, UV radiation, electron beam exposure or moisture or other means of curing, leading to the irreversible formation of a crosslinked network of covalent bonds. Those materials having lost their initial thermoplastic behaviour are herein also understood as thermoplastic materials 120.

Without wishing to be bound by theory it has been found that those thermoplastic compositions are most useful for immobilizing the absorbent polymer material 110, which combines good cohesion and good adhesion behaviour. Good adhesion is critical to ensure that the thermoplastic layer 120 maintains good contact with the absorbent polymer material 110 and in particular with the substrate 100. Good adhesion is a challenge, namely when a non-woven substrate is used. Good cohesion ensures that the adhesive does not break, in particular in response to external forces, and namely in response to strain. The adhesive is subject to external forces when the absorbent product has acquired liquid, which is then stored in the absorbent polymer material 110 which in response swells. A preferred adhesive will allow for such swelling, without breaking and without imparting too many compressive forces, which would restrain the absorbent polymer material 110 from swelling. Importantly, in accordance with the present invention the adhesive should not break, which would deteriorate the wet immobilization. Preferred thermoplastic compositions meeting these requirements have the following features:

The thermoplastic composition may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic composition may be a hot melt adhesive comprising at least one thermoplastic polymer in combination with other thermoplastic diluents such as tackifying resins, plasticizers and additives such as antioxidants.

The thermoplastic polymer has typically a molecular weight (Mw) of more than 10,000 and a glass transition temperature (Tg) usually below room temperature. Typical concentrations of the polymer in a hot melt are in the range of 20-40% by weight. A wide variety of thermoplastic polymers are suitable for use in the present invention. Such thermoplastic polymers are preferably water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alphaolefins.

The resin has typically a Mw below 5,000 and a Tg usually above room temperature, typical concentrations of the resin in a hot melt are in the range of 30-60%. The plasticizer has a low Mw of typically less than 1,000 and a Tg below room temperature, a typical concentration is 0-15%.

Preferably the adhesive is present in the forms of fibres throughout the core, i.e., the adhesive is fiberized. Preferably, the fibres will have an average thickness of 1-50 micrometer and an average length of 5 mm to 50 cm.

To improve the adhesion of the thermoplastic material 120 to the substrate layer 100 or to any other layer, in particular any other non-woven layer, such layers may be pre-treated with an auxiliary adhesive.

Preferably, the adhesive will meet at least one, and more preferably several or all of the following parameters:

A preferred adhesive will have a storage modulus G' measured at 20° C. of at least 30,000 Pa and less than 300,000 Pa preferably less than 200,000 Pa, more preferably less than 100,000 Pa. The storage modulus G' at 20° C. is a measure for the permanent "tackiness" or permanent adhesion of the thermoplastic material used. Good adhesion will ensure a good and permanent contact between the thermoplastic material and for example the substrate layer 100. In a further aspect, the storage modulus G' measured at 60° C. should be less than 300,000 Pa and more than 18,000 Pa, preferably more than 24,000 Pa, most preferably more than 30,000. The storage modulus measured at 60° C. is a measure for the form stability of the thermoplastic material at elevated ambient temperatures. This value is particularly important if the absorbent product is used in a hot climate where the thermoplastic composition would lose its integrity if the storage modulus G' at 60° C. is not sufficiently high.

In a further aspect, the loss angle tan Delta of the adhesive at 60° C. should be below the value of 1, preferably below the value of 0.5. The loss angle tan Delta at 60° C. is correlated with the liquid character of an adhesive at elevated ambient temperatures. The lower tan Delta, the more an adhesive behaves like a solid rather than a liquid, i.e., the lower its tendency to flow or to migrate and the lower the tendency of an adhesive superstructure as described herein to deteriorate or even to collapse over time. This value is hence particularly important if the absorbent article is used in a hot climate.

In a further aspect, the preferred adhesive should have a glass transition temperature $T_g$ of less than 25° C., preferably less than 22° C., more preferably less than 18° C., and most preferably less than 15° C. A low glass transition temperature $T_g$ is beneficial for good adhesion. In a further aspect a low glass transition temperature Tg ensures that the adhesive thermoplastic material does not become to brittle.

In yet a further aspect, a preferred adhesive will have a sufficiently high cross-over temperature $T_x$. A sufficiently high cross-over temperature $T_x$ has been found beneficial for high temperature stability of the thermoplastic layer and hence it ensures good performance of the absorbent product and in particular good wet immobilization even under conditions of hot climates and high temperatures. Therefore, $T_x$ should preferably be above 80° C., more preferably above 85° C., and most preferably above 90° C.

In a further important aspect, preferred adhesives in accordance with the present invention will have a sufficient cohesive strength parameter γ. The cohesive strength parameter γ is measured using the rheological creep test as described hereinafter. A sufficiently low cohesive strength parameter γ is representative of elastic adhesive which, for example, can be stretched without tearing. If a stress of τ=1000 Pa is applied, the cohesive strength parameter γ is preferably less than 100%, more preferably less than 90%, and most preferably less than 75%. For a stress of τ=125,000 Pa, the cohesive strength parameter γ is preferably less than 1200%, more preferably less than 1000%, and most preferably less than 800%.

A highly preferred adhesive useful as a thermoplastic material 120 as described herein will meet most or all of the above parameters. Specific care must be taken to ensure that the adhesive provides good cohesion and good adhesion at the same time.

The process for producing preferred absorbent cores 28 in accordance with the present invention comprises the following steps:

The absorbent core 28 is laid down onto a laydown drum, which presents an uneven surface. In a first process step the substrate layer 100 is laid on to the uneven surface. Due to gravity, or preferably by using a vacuum means, the substrate layer material will follow the contours of the uneven surface and thereby the substrate layer material will assume a mountain and valley shape. Onto this substrate layer 100 absorbent polymeric material is disposed by means known in the art. The absorbent polymer material will accumulate in the valleys presented by the substrate layer 100. In a further process step a hot melt adhesive is placed onto the absorbent polymer material.

While any adhesive application means known in the art can be used to place the hot melt adhesive on to the absorbent polymer material, the hot melt adhesive is preferably applied by a nozzle system. Preferably, a nozzle system is utilised, which can provide a relatively thin but wide curtain of adhesive. This curtain of adhesive is than placed onto the substrate layer 100 and the absorbent polymer material. As the mountain tops of the substrate layer 100 are less covered by absorbent polymer material the adhesive will make contact with these areas of the substrate layer.

In an optional further process step a cover layer 130 is placed upon the substrate layer 100, the absorbent polymer material and the hot melt adhesive layer. The cover layer 130 will be in adhesive contact with the substrate layer 100 in the areas of junction 140. In these areas of junction 140 the adhesive is in direct contact with the substrate layer 100. The cover layer 130 will typically not be in adhesive contact with the substrate layer 100 where the valleys of the substrate layer 100 are filled with absorbent polymer material.

Alternatively the cover layer 130 can be laid down onto a drum with an uneven surface and the substrate layer 100 can be added in a consecutive process step. The embodiment shown in FIG. 4 could be produced by such a process.

In one alternative embodiment, the cover layer 130 and the substrate layer 100 are provided from a unitary sheet of material. The placing of the cover layer 130 onto the substrate layer 100 will then involve the folding of the unitary piece of material.

Hence, the uneven surface of the lay-down system, which preferably is a lay-down drum, typically determines the distribution of absorbent polymeric material throughout the storage layer 60 and likewise determines the pattern of areas of junction 140. Alternatively, the distribution of absorbent polymeric material may be influenced by vacuum means.

Preferably the distribution of absorbent polymeric material is profiled and most preferably profiled in the longitudinal direction. Hence, along the longitudinal axis of the absorbent core, which is normally coincident with the longitudinal axis of the absorbent article, for example of the diaper, the basis weight of the absorbent polymer material will change. Preferably the basis weight of absorbent polymer material in at least one freely selected first square measuring 1 cm×1 cm is at least 10%, or 20%, or 30%, 40% or 50% higher than the basis weight of absorbent polymer material in at least one freely selected second square measuring 1 cm×1 cm. Preferably the criterion is met if the first and the second square are centred about the longitudinal axis.

Optionally, the absorbent core can also comprise an absorbent fibrous material, for example cellulose fibres. This fibrous material can be pre-mixed with the absorbent polymeric material and be laid down in one process step or it can alternatively be laid-down in separate process steps.

It has been found beneficial to use a particulate absorbent polymer material for absorbent cores made in the present invention. Without wishing to be bound by theory it is believed that such material, even in the swollen state, i.e., when liquid has been absorbed, does not substantially obstruct the liquid flow throughout the material, especially when the permeability as expressed by the saline flow conductivity of the absorbent polymer material is greater than 10, 20, 30 or 40 SFC-units, where 1 SFC unit is $1\times10^{-7}$ $(cm^3\times s)/g$. Saline flow conductivity is a parameter well recognised in the art and is to be measured in accordance with the test disclosed in U.S. Pat. No. 5,599,335.

As to achieve a sufficient absorbent capacity in a preferred absorbent article according to the present invention and especially if the absorbent article is a diaper or an adult incontinence product, superabsorbent polymer material will be present with a basis weight of more than 50, 100, 200, 300, 400, 500, 600, 700, 800 or 900 $g/m^2$.

Preferred articles according to the present invention achieve a relatively narrow crotch width, which increases the wearing comfort. A preferred article according to the present invention achieves a crotch width of less than 100 mm, 90 mm, 80 mm, 70 mm, 60 mm or even less than 50 mm. Hence, preferably an absorbent core according to the present invention has a crotch width as measured along a transversal line which is positioned at equal distance to the front edge and the rear edge of the core which is of less than 100 mm, 90 mm, 80 mm, 70 mm, 60 mm or even less than 50 mm. It has been found that for most absorbent articles the liquid discharge occurs predominately in the front half. The front half of the absorbent core should therefore comprise most of the absorbent capacity of the core. Preferably the front half of said absorbent core comprises more than 60% of the absorbent capacity, more preferably more than 65%, 70%, 75%, 80%, 85%, or 90%.

All patents and patent applications (including any patents which issue thereon) assigned to the Procter & Gamble Company referred to herein are hereby incorporated by reference to the extent that it is consistent herewith.

Rheological Creep Test

Equipment:

AR 2000 Rheometer by TA Instruments as described below

Balance

Rheometer:

A test set up for carrying out the creep test employs the AR 2000 Rheometer by TA Instruments. Other rheometers are available on the market, which yield substantially the same test results. FIG. 7 provides a schematic representation of the rheometer (400). The rheometer is capable of applying a shear stress to the adhesive and measuring the resulting strain (shear deformation) response at constant temperature. The adhesive is placed between a Peltier-element acting as lower, fixed plate (410) and an upper plate (420) with a radius R of 10 mm, which is connected to the drive shaft of a motor to generate the shear stress. The gap between both plates has a height H of 1500 micron. The Peltier-element enables to control the temperature of the material (±0.5° C.).

Sample Preparation:

Homogenize the adhesive at 150° C.-175° C. (depending on type of adhesive) for 1 hour in a lab oven Stir occasionally to ensure proper mixing of wrap and adhesive, but prevent formation of air bubbles After homogenization in the oven pour the sample on silicone paper for cooling After the material is cooled to RT (room temperature), weigh approximately 0.6 g of adhesive for the creep test and place the material on the Peltier-plate Test Execution:

Melt the adhesive at 120° C. (or higher if necessary) on the Peltier-plate

As soon as the adhesive is completely molten, lower the upper plate to a gap of 1500 micron to bring it into proper contact with the adhesive melt Remove excessive material Set the temperature to the measurement temperature of 35° C.

Set the conditioning time to 20 min to ensure thermal equilibrium between Peltier, adhesive and upper plate Set constant measurement stress τ (e.g., 10,000 Pa resp. 125,000 Pa) to be applied immediately to the adhesive at the beginning of the retardation step Set the retardation time to 5 min Set the stress to zero for immediate removal of stress at the beginning of the recovery step Set the recovery time to 5 min After the test is completed, melt the adhesive, lift the upper plate and remove the adhesive from both Peltier and upper plate.

Set the temperature back to the measurement temperature or stand-by temperature (RT)

Result Reporting:

Report the strain in % (γ value, herein referred to as cohesive strength parameter) as a function of temperature and stress after 5 min application of stress (at the end of the retardation step), e.g., at 35° C. and 10,000 Pa resp. 35° C. and 125,000 PA as described herein.

Dynamical Mechanical Analysis (DMA)—Temperature Sweep

Equipment:

AR 2000 Rheometer by TA Instruments as described below

Balance

Rheometer:

A test set up for carrying out the temperature sweep comprises the AR 2000 Rheometer by TA Instruments as described herein. Other rheometers are available on the market, which yield substantially the same test results. FIG. 7 provides a schematic representation of the rheometer (400). The rheometer is capable of applying a shear stress to the adhesive and measuring the resulting strain (shear deformation) response at constant temperature.

The rheometer is capable of applying a small oscillatory stress to achieve a constant oscillatory strain within the linear viscoelastic region of the adhesive (e.g., 0.05%). The instrument enables the measurement of resulting Storage Modulus, Loss Modulus and the phase shift between stress and strain (Loss Factor) in dependence of temperature. The oscillation frequency is 1 Hz. The adhesive is placed between a Peltier-element acting as lower, fixed plate (410) and an upper plate (420) with a radius R of 10 mm, which is connected to the drive shaft of a motor to generate the shear stress. The gap between both plates has a height H of 1500 micron. The Peltier-element enables to control the temperature of the material (±0.5° C.).

Sample Preparation:

Homogenize the adhesive at 150° C.-175° C. (depending on type of adhesive) for 1 hour in a lab oven.

Stir occasionally to ensure proper mixing of wrap and adhesive, but prevent formation of air bubbles.

After homogenization in the oven pour the sample on silicone paper for cooling.

After the material is cooled to RT, weigh approximately 0.6 g of adhesive the temperature sweep and place the material on the Peltier-plate.

Test Execution:

Melt the adhesive at 120° C. (or higher if necessary) on the Peltier-plate

As soon as the adhesive is completely molten, lower the upper plate to a gap of 1500 micron to bring it into proper contact with the adhesive melt Remove excessive material and set the temperature to the measurement start temperature (e.g., 150° C., depending on the temperature range of interest→see below)

Set the temperature to the start temperature depending on the temperature range at which the rheological properties of the adhesive need to be determined (e.g., 150° C., in any case start with highest temperature)

Set the conditioning time to 20 min to ensure thermal equilibrium between Peltier, adhesive and upper plate Set the start temperature (see above)

Set the constant measurement strain (e.g., 0.05%)

Set the constant frequency (e.g., 1 Hz)

Set the cooling rate (e.g., 2° C./min)

Set the end temperature (e.g., −5° C.) depending on the temperature range at which the rheological properties of the adhesive need to be determined and depending on the cooling capacity of the Peltier Set the temperature to RT After the test is completed, melt the adhesive, lift the upper plate and remove the adhesive from both Peltier and upper plate.

Set the temperature back to RT

Result Reporting

Report the Storage Modulus G' in Pa and the Loss Factor tan Delta (dimensionless) at 20° C. and 60° C.

Report the glass transition temperature Tg in ° C. (inflection point of G')

Report the cross-over temperature Tx in ° C. at which G' equals G" at the end of the rubber plateau towards higher temperature (beginning of terminal zone)

Determination of Surface Tension

The surface tension (unit: mN/m) is determined according to the following test.

Apparatus:

Equipment: K10 tensiometer provided by Krüss GmbH, Germany or equivalent. The vessel elevation speed should be 4 mm/min. Liquid surface height should be sensed automatically when using a plate or a ring. The equipment must be able to adjust the sample position automatically to the correct height. Precision of test should be +/−0.1 mN/m.

Procedure:
1. Pouring 40 ml of saline (0.9 wt % NaCl in deionized water) into a cleaned beaker.
2. Testing the surface tension with a platinum ring or a platinum plate. The surface tension should be 71-72 mN/m at 20° C.
3. Cleaning the beaker with deionized water and isopropanol and burning it out with a gas burner for a few seconds. Waiting until equilibrate to room temperature is reached.
4. Placing 10 60×60 mm pieces of test nonwoven into a cleaned beaker. The nonwoven should have a basis weight of at least 10 gsm.
5. Adding 40 ml of saline (0.9 wt % NaCl in deionized water).
6. Stirring with a clean surfactant-free plastic stick for 10 seconds.
7. Letting the solution with nonwoven stand for 5 minutes.
8. Stirring again for 10 seconds.
9. Removing the nonwoven from the solvent with a clean surfactant-free plastic stick.
10. Letting the solution stand for 10 minutes.
11. Testing surface tension with a platinum plate or platinum ring.

Determination of Strike Through

The test is carried out based on Edana Method 150.3-96 (February 1996) Liquid Strike Through Time. As a major modification compared to the Edana Method, the test described below not only measures the first gush but also several subsequent gushes.

Apparatus:
Lister Strike Through Equipment:
Funnel fitted with magnetic valve: Rate of discharge of 25 ml in 3.5 (±0.25) seconds
Strike through plate: Constructed of 25 mm thick acrylic glass. The total weight of the plate must be 500 g. The electrodes should be of non-corrosive material. The electrodes are set in (4.0 mm×7.0 mm) cross section grooves, cut in the base of the plate and fixed with quick setting epoxy resin.
Base plate: A square of acrylic glass 125 mm×125 mm approximately.
Ring stand to support the funnel
Electronic Timer measuring to 0.01 seconds
Burette with 50 ml capacity
Core filter paper Ahlström Grade 989 or equivalent (average Strike Through time 1.7 s+−0.3 s, dimensions: 10×10 cm)

Procedure:
1. Carefully cutting the required number of samples, 12.5 cm×12.5 cm touching the sample only at the edge of the sample.
2. Taking 10 plies of core filter paper.
3. Placing one sample on the set of 10 plies of filter paper on the base plate. The sample should be positioned on the filter paper in such a way that the side of the nonwoven, which is intended to face the user's skin (when applied in an absorbent article) is uppermost.
4. Placing the strike through plate on top with the center of the plate over the center of the test piece.
5. Centering the burette and the funnel over the plate.
6. Ensuring that the electrodes are connected to the timer. Switching on the timer and set the clock to zero.
7. Filling the burette with saline solution (0.9 wt % NaCl in deionized water).
8. Keeping the discharge valve of the funnel closed and run 5.0 ml of liquid (=one gush) from the burette into the funnel.
9. Opening the magnetic valve of the funnel to discharge 5.0 ml of liquid. The initial flow of liquid will complete the electrical circuit and start the timer. It will stop when the liquid has penetrated into the pad and fallen below the level of the electrodes in the strike through plate.
10. Recording the time indicated on the electronic timer.
11. Waiting for 60 seconds and continuing as of point 6 for the second, the third gush and any subsequent gush, with each gush comprising 5 ml of liquid.
12. Report: Time for the $1^{st}$, $2^{nd}$ and any subsequent gush in seconds.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
a chassis including a topsheet and a backsheet; and
an absorbent core located between the topsheet and the backsheet;
wherein the absorbent core comprises a substrate layer; a first discontinuous layer of absorbent material deposited on the substrate layer; a second substrate layer and a second discontinuous layer of absorbent material deposited on the second substrate layer;
wherein in the first discontinuous layer of absorbent material comprises first openings and wherein the second discontinuous layer of absorbent material comprises second openings, and wherein the first and second substrate layers are combined together such that the first openings are offset from the second openings.

2. The disposable absorbent article of claim 1, wherein the absorbent core further comprises a thermoplastic material and wherein the thermoplastic material is a hot melt adhesive.

3. The disposable absorbent article of claim 2, wherein the thermoplastic material comprises a net-like structure.

4. The disposable absorbent article of claim 1, wherein the substrate layer further comprises an auxiliary adhesive.

5. The disposable absorbent article of claim 1 wherein the first openings and/or the second openings comprise a largest span of less than 10 mm.

6. The disposable absorbent article of claim 1 wherein the first discontinuous layer of absorbent material comprises absorbent polymer material.

7. The disposable absorbent article of claim 6 wherein the first discontinuous layer of absorbent material further comprises airfelt material.

8. A disposable absorbent article comprising:
a chassis including a topsheet and a backsheet; and
an absorbent core located between the topsheet and the backsheet;
wherein the absorbent core comprises a substrate layer; a first discontinuous layer of absorbent material deposited on the substrate layer; a second substrate layer and a second layer of absorbent material deposited on the second substrate layer;
wherein in the first discontinuous layer of absorbent material comprises a first opening disposed between two areas of absorbent material and wherein the first and second substrate layers are combined together such that the first opening faces absorbent material in the second layer of absorbent material.

9. The disposable absorbent article of claim 8 wherein the second layer of absorbent material comprises a discontinuous layer of absorbent material having a second opening, and wherein the first and second substrate layers are combined together such that the second opening faces abosorbent material in the first discontinuous layer of absorbent material.

10. The disposable absorbent article of claim 8 wherein the first openings and/or the second openings comprise a largest span of less than 10 mm.

11. The disposable absorbent article of claim 8 wherein the first discontinuous layer of absorbent material comprises absorbent polymer material.

12. The disposable absorbent article of claim 11 wherein the first discontinuous layer of absorbent material further comprises airfelt material.

\* \* \* \* \*